US005567814A

United States Patent [19]

Flynn et al.

[11] Patent Number: 5,567,814

[45] Date of Patent: Oct. 22, 1996

[54] 2-SUBSTITUTED INDANE-2-MERCAPTOACETYLAMIDE DISULFIDE DERIVATIVES USEFUL AS INHIBITORS OF ENKEPHALINASE AND ACE

[75] Inventors: Gary A. Flynn; Douglas W. Beight; Alan M. Warshawsky; Shujaath Mehdi; John F. French; John H. Kehne, all of Cincinnati, Ohio

[73] Assignee: Merrell Pharmaceuticals Inc., Cincinnati, Ohio

[21] Appl. No.: 397,304

[22] Filed: Mar. 2, 1995

Related U.S. Application Data

[62] Division of Ser. No. 195,526, Feb. 14, 1994, abandoned.

[51] Int. Cl.⁶ ............................ A61K 31/33; C07D 223/10
[52] U.S. Cl. ............................ 540/521; 540/522; 514/214
[58] Field of Search ................................ 540/521, 522

[56] References Cited

U.S. PATENT DOCUMENTS

| | | | |
|---|---|---|---|
| 3,334,091 | 7/1967 | Houlihan | 260/243 |
| 3,334,095 | 8/1967 | Houluhan | 260/244 |
| 4,080,449 | 3/1978 | Croisier et al. | 424/244 |
| 4,320,057 | 3/1982 | Freed et al. | 260/239.3 B |
| 4,391,752 | 7/1983 | Crossley | 260/239.3 B |
| 4,399,136 | 8/1983 | Hassall et al. | 224/250 |
| 4,415,496 | 11/1983 | Harris et al. | 540/239.3 B |
| 4,487,929 | 12/1984 | Hassall et al. | 544/224 |
| 4,512,924 | 4/1985 | Attwoood et al. | 260/243.3 |
| 4,584,294 | 4/1986 | Ruyle | 514/214 |
| 4,658,024 | 4/1987 | Attwood et al. | 540/500 |
| 4,692,438 | 9/1987 | Hassall et al. | 544/238 |
| 4,716,232 | 12/1987 | Ternansky | 548/112 |
| 4,734,504 | 3/1988 | Holmes | 548/112 |
| 4,734,505 | 3/1988 | Holmes | 548/364 |
| 4,762,924 | 8/1988 | Hassall et al. | 540/501 |
| 4,772,701 | 9/1988 | Attwood et al. | 544/235 |
| 4,782,149 | 11/1988 | Lawton et al. | 544/224 |
| 4,785,093 | 11/1988 | Hassall et al. | 544/460 |
| 4,808,713 | 2/1989 | Attwood et al. | 540/487 |
| 4,824,832 | 4/1989 | Flynn et al. | 514/214 |
| 4,826,980 | 5/1989 | Hassall et al. | 544/224 |
| 4,973,585 | 11/1990 | Flynn et al. | 514/214 |
| 5,238,932 | 8/1993 | Flynn et al. | 540/521 |

FOREIGN PATENT DOCUMENTS

| | | | |
|---|---|---|---|
| 0128728 | 12/1984 | European Pat. Off. | 564/154 |
| 0249224 | 12/1987 | European Pat. Off. | 540/522 |
| 0249223 | 12/1987 | European Pat. Off. | 540/522 |
| 0322914 | 12/1988 | European Pat. Off. | 540/522 |
| 0481522 | 4/1992 | European Pat. Off. | 540/522 |
| 0492369 | 7/1992 | European Pat. Off. | 540/522 |
| 0533084 | 9/1992 | European Pat. Off. | 540/522 |
| 0599444 | 6/1994 | European Pat. Off. | 540/490 |
| 9108195 | 6/1991 | WIPO | 564/154 |
| 9109840 | 7/1991 | WIPO | 564/154 |
| 9302099 | 2/1993 | WIPO | 548/572 |

OTHER PUBLICATIONS

Flynn, et al., J. Am. Chem. Soc. 109, 7914 (1987).
Flynn, et al., Peptide Chemistry (1987); T. Shiba & Sakakibara (ed.), Protein Research Foundation, Osaka (1988).
Flynn, et al., Tetrahedron Letters, vol. 31 (6), 815–88 (1990).
Attwood, et al., J. Chem. Soc. Perkin Trans. I, pp. 1011–1019 (1986).
Natoff, et al., Drugs of the Future, vol. 12 (5): 475–483 (1987).
Powell Jerry S. et al., Journal of American College of Cardiology, vol. 17, No. 6, pp. 137B–142B (May 1991).
Davis, Harry R. et al., Supplement I Circulation, vol. 86, No. 4 p. I–220(0873), (Oct. 1992).
W. H. Parsons et al. Biochemical and Biophysical Research Communications, vol. 117, No. 1, 1993 (Nov. 30, 1983).
Burkholder, et al. Bioorganic and Medical Chem. Letters, vol. 3, No. 2, pp. 231–234, 1993.
Flynn et al., J. Med. Chem.1993, 36 2420–2423.
J. Med. Chem. 1992, 35, 823–832, Timothy D. Ocain et al.
Bioorganic and Medical Chem. Letters, vol. 1, 309, 1991.
Fournie–Zaluski, Marie–Claude et al., J. Med. Chem., 1992 vol. 35, pp. 2473–2481.
Fournie–Zaluski, Marie–Claude et al., J. Med. Chem., 1992 vol. 35, pp. 1259–1266.
French, John F., Jour. of Pharm and Exper. Therapeutics, vol. 268, No. 1, pp. 180–18.6 (1994).

Primary Examiner—Robert T. Bond
Attorney, Agent, or Firm—David M. Stemerick

[57] ABSTRACT

The present invention relates to certain novel 2-substituted indane-2-mercaptoacetylamide disulfide derivatives useful as inhibitors of enkephalinase and of ACE.

11 Claims, No Drawings

5,567,814

2-SUBSTITUTED INDANE-2-MERCAPTOACETYLAMIDE DISULFIDE DERIVATIVES USEFUL AS INHIBITORS OF ENKEPHALINASE AND ACE

This is a division of application Ser. No. 08/195,526, filed Feb. 14, 1994, now abandoned which is herein incorporated by reference.

BACKGROUND OF THE INVENTION

Enkephalinase or, more specifically, endopeptidase-24.11, is a mammalian ectoenzyme which is involved in the metabolic degradation of certain circulating regulatory peptides. This enzyme, which is a $Zn^{+2}$-metallopeptidase, exerts its effect by cleaving the extracellular peptides at the amino group of hydrophobic residues and thus inactivates the peptides as regulatory messengers.

Enkephalinase is involved in the metabolic degradation of a variety of circulating regulatory peptides including endorphins, such as β-endorphin and the enkephalins, atrial natriuretic peptide (ANP), and other circulating regulatory peptides.

Endorphins are naturally-occurring polypeptides which bind to opiate receptors in various areas of the brain and thereby provide an analgesic effect by raising the pain threshold. Endorphins occur in various forms including α-endorphin, β-endorphin, γ-endorphin as well as the enkephalins. The enkephalins, i.e., Met-enkephalin and Leu-enkephalin, are pentapeptides which occur in nerve endings of brain tissue, spinal cord and the gastrointestinal tract. Like the other endorphins, the enkephalins provide an analgesic effect by binding to the opiate receptors in the brain. By inhibiting enkephalinase, the metabolic degradation of the naturally-occurring endorphins and enkephalins are inhibited, thereby providing a potent endorphin- or enkephalin-mediated analgesic effect. Inhibition of enkephalinase would therefore be useful in a patient suffering from acute or chronic pain. Inhibition of enkephalinase would also be useful in providing an antidepressant effect and in providing a reduction in severity of withdrawal symptoms associated with termination of opiate or morphine administration. In addition, inhibition of enkephalinase would also be useful in the treatment of irritable bowel syndrome.

ANP refers to a family of naturally-occurring peptides which are involved in the homeostatic regulation of blood pressure, as well as sodium and water levels. ANP have been found to vary in length from about 21 to about 126 amino acids with a common structural feature being one or more disulfide-looped sequences of 17 amino acids with various amino- and carboxy-terminal sequences attached to the cysteine moiety. ANP have been found to bind to specific binding sites in various tissues including kidney, adrenal, aorta, and vascular smooth muscle with affinities ranging from about 50 pico-molar (pM) to about 500 nano-molar (nM) [Needleman, Hypertension 7, 469 (1985)]. In addition, it is believed that ANP binds to specific receptors in the brain and possibly serves as a neuromodulator as well as a conventional peripheral hormone.

The biological properties of ANP involve potent diuretic/natriuretic and vasodilatory/hypotensive effects as well as an inhibitory effect on renin and aldosterone secretion [deBold, Science 230, 767 (1985)]. By inhibiting enkephalinase, the metabolic degradation of the naturally-occurring ANP are inhibited, thereby providing a potent ANP-mediated diuretic, natriuretic, hypotensive, hypoaldosteronemic effects. Inhibition of enkephalinase would therefore be useful in a patient suffering from disease states characterized by abnormalities in fluid, electrolyte, blood pressure, intraocular pressure, renin, or aldosterone homeostasis, such as, but not limited to, hypertension, renal diseases, hyperaldosteronemia, cardiac hypertrophy, glaucoma and congestive heart failure.

In addition, the compounds of the present invention are inhibitors of Angiotensin-Converting Enzyme (ACE). ACE is a peptidyl dipeptidase which catalyzes the conversion of angiotensin I to angiotensin II. Angiotensin II is a vasoconstrictor which also stimulates aldosterone secretion by the adrenal cortex. Inhibition of ACE would therefore be useful in a patient suffering from disease states such as hypertension and congestive heart failure [See William W. Douglas, "Polypeptides—Angiotensin, Plasma Kinins, and Others", Chapter 27, in *Goodman and Gillman's the Pharmacological Basis of Therapeutics*, 7th edition, 1985, pp. 652-3, MacMillan Publishing Co., New York, N.Y.]. In addition, it has been discovered that ACE inhibitors are useful in treating cognitive disorders [German Application No. 3901-291-A, published Aug. 3, 1989].

In addition, the compounds of the present invention are useful as inhibitors of smooth cell proliferation. Smooth muscle cell proliferation in the intima of muscular arteries is a primary cause of vascular stenosis in arteriosclerosis, after vascular surgery, and after coronary angioplasy. Several animal studies have indicated the renin-angiotensin system plays an important role in this vascular response to injury. Chronic treatment with angiotensin converting enzyme (ACE) inhibitors reduced myointimal thickening following balloon injury in rat carotid artery or aorta. Powell, J.S., Muller, R.K.M. and Baumgartner, H.R.; Suppression of the vascular response to injury: The role of angiotensin-converting enzyme inhibitors. *J. Am. Coll. Cardiol.* 17:137B–42B, 1991. More recently, atrial natruiuretic peptide (ANP) has been found to decrease myointimal proliferation. ANP is rapidly metabolized by receptor mediated clearance and by neutral endopeptidase (NEP). Inhibition of NEP significantly reduces proliferation in the balloon-injured rabbit vasculature. Davis, H. R., McGregor, D. C., Hoos, L., Mullins, D. E. and Sybertz, E. J.: Atrial naturiuretic factor and the neutral endopeptidase inhibitor SCH42495 prevent myointimal proliferation after vascular injury. Circ. 86:I-220, 1992. These studies imply that a dual inhibitor of ACE and NEP should be therapeutically useful in the treatment of conditions which require inhibition of smooth cell proliferation. Davis and Sybertz, European Patent Application 533084-A1, Mar. 24, 1993.

SUMMARY OF THE INVENTION

The present invention provides novel compounds of the Formula (I)

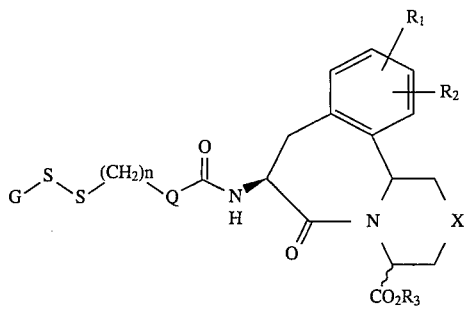

Formula (I)

wherein n is an integer from 0 to 3;

$R_1$ and $R_2$ are each time taken independently chosen from the group consisting of; hydrogen, hydroxy, —$OR_4$ wherein $R_4$ is a $C_1$-$C_4$ alkyl or an Ar—Y— group wherein Ar is aryl and Y is a $C_0$-$C_4$ alkyl; or, where $R_1$ and $R_2$ are attached to adjacent carbon atoms, $R_1$ and $R_2$ can be taken together with said adjacent carbons to form a benzene ring or methylenedioxy;

$R_3$ is hydrogen, $C_1$-$C_4$ alkyl, —$CH_2O$—$C(O)C(CH_3)_3$;

X is —$(CH_2)_p$—, O, S, $NR_5$, or $NC(O)R_6$ wherein p is an integer 0 or 1, $R_5$ is hydrogen, a $C_1$-$C_4$ alkyl, or an Ar—Y— group, and $R_6$ is —$CF_3$, $C_1$-$C_{10}$ alkyl, or an Ar—Y— group;

Q is a alkylene radical chosen from the group

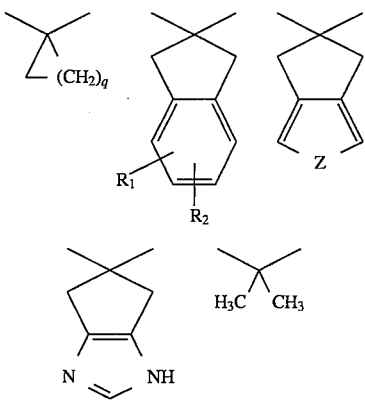

wherein q is an integer from 1 to 5 and Z is O, S, NH;

G is a radical chosen from the group;

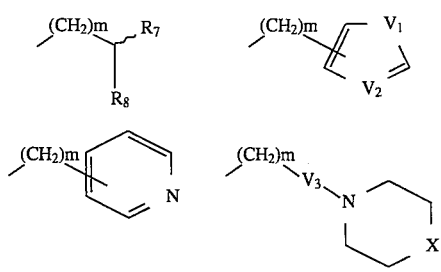

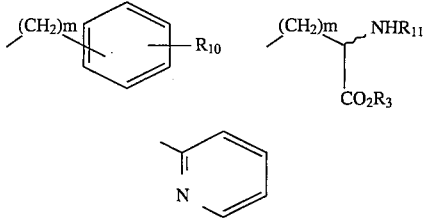

wherein m is an integer from 1 to 3;

$R_7$ is hydrogen, $C_1$-$C_6$ alkyl, —$CH_2CH_2S(O)_kCH_3$, or Ar—Y— wherein k is an integer form 0 to 2;

$R_8$ is hydrogen, hydroxy, amino, $C_1$-$C_6$ alkyl, N-methylamino, N,N-dimethylamino, —$CO_2R_3$—$OC(O)R_9$ wherein $R_9$ is hydrogen, $C_1$-$C_6$ alkyl, or phenyl;

$R_{10}$ is 1 or 2 substituents independently chosen from the group consisting of; hydrogen, $C_1$-$C_4$ alkyl, $C_1$-$C_4$ alkoxy, or halogen;

$R_{11}$ is hydrogen, $C_1$-$C_6$ alkyl, or Ar—Y— group;

$V_1$ is O, S, or NH;

$V_2$ is N or CH;

$V_3$ is a direct bond or —C(O)—;

or stereoisomers or pharmaceutically acceptable salts thereof.

The present invention further provides a method of inhibiting enkephalinase in a patient in need thereof comprising administering to said patient an effective enkephalinase inhibitory amount of a compound of Formula (I). The present invention also provides a method of inhibiting ACE in a patient in need thereof comprising administering to said patient an effective ACE inhibitory amount of a compound of Formula (I).

In addition, the present invention provides a composition comprising an assayable amount of a compound of Formula (I) in admixture or otherwise in association with an inert carrier. The present invention also provides a pharmaceutical composition comprising an effective inhibitory amount of a compound of Formula (I) in admixture or otherwise in association with one or more pharmaceutically acceptable carriers or excipients.

DETAILED DESCRIPTION OF THE INVENTION

As used in this application:

a) the term "$C_1$-$C_6$ alkyl" refers to a saturated straight or branched chain hydrocarbyl radical of from one to six carbon atoms and includes methyl, ethyl, propyl, isopropyl, n-butyl, isobutyl, tertiary butyl, n-pentyl, cyclopentyl, n-hexyl, cyclo-hexyl and the like;

b) the term "$C_1$-$C_4$ alkyl" refers to a saturated straight or branched chain hydrocarbyl radical of from one to six carbon atoms and includes methyl, ethyl, propyl, isopropyl, n-butyl, isobutyl, tertiary butyl;

c) the designation "⊳" refers to a bond that protrudes forward out of the plane of the page;

d) the designation "⊲" refers to a bond that protrudes backward out of the plane of the page;

e) the designation "~" refers to a bond for which the stereochemistry is not designated;

f) the term "halogen" refers to a fluorine atom, chlorine atom, bromine atom, or iodine atom;

g) the terms "$C_1-C_8$ alkyl" and "$C_1-C_{10}$ alkyl" refer to saturated straight or branched chain hydrocarbyl radicals of one to eight and one to ten carbon atoms, respectively, including methyl, ethyl, propyl, isopropyl, n-butyl, isobutyl, tertiary butyl, pentyl, isopentyl, hexyl, 2,3-dimethyl-2-butyl, heptyl, 2,2-dimethyl-3-pentyl, 2-methyl-2-hexyl, octyl, 4-methyl-3-heptyl and the like;

h) the term "$C_1-C_4$ alkoxy" refer to a straight or branched alkoxy group containing from 1 to 4 carbon atoms, such as methoxy, ethoxy, n-propoxy, isopropoxy, n-butoxy, isobutoxy, t-butoxy, etc;

i) the designation "—C(O)—" refers to a carbonyl group of the formula:

j) the term "Ar—Y—" refers to a radical wherein Ar is an aryl group and Y is a $C_0-C_4$ alkyl;

k) the term "$C_0-C_4$ alkyl" refers to a saturated straight or branched chain hydrocarbyl radical of zero to four carbon atoms and includes a bond, methyl, ethyl, propyl, isopropyl, n-butyl, isobutyl, tertiary butyl and the like;

l) the term "Ar" or "aryl group" refers to a phenyl or naphthyl group unsubstituted or substituted with from one to three substituents selected from the group consisting of methylenedioxy, hydroxy, $C_1-C_4$ alkoxy, fluoro and chloro; specifically included within the scope of the term "arylalkyl" are phenyl, naphthyl, naphthylmethyl, phenylmethyl or benzyl, phenylethyl, p-methoxybenzyl, 3,4-methylenedioxybenzyl, p-fluorobenzyl and p-chlorobenzyl;

m) the term "protected amino" refers to either a —$NHPg_1$ or —$NPg_2Pg_3$ wherein $Pg_1$, $Pg_2$, and $Pg_3$ are amino protecting groups as described in *Protecting Groups in Organic Synthesis* by T. Greene as is well known and appreciated by those skilled in the art which allow for the formation of disulfides and then are removable to afford compounds of Formula (I) in which $R_8$ in amino;

n) the term "Pg" refers to protecting group;

o) the term "pharmaceutically acceptable salts" refers to either acid addition salts or to base addition salts.

The expression "pharmaceutically acceptable acid addition salts" is intended to apply to any non-toxic organic or inorganic acid addition salt of a compound of Formula (I) or any of its intermediates. Illustrative inorganic acids which form suitable salts include hydrochloric, hydrobromic, sulphuric, and phosphoric acid and acid metal salts such as sodium monohydrogen orthophosphate, and potassium hydrogen sulfate. Illustrative organic acids which form suitable salts include the mono-, di-, and tricarboxylic acids. Illustrative of such acids are for example, acetic, glycolic, lactic, pyruvic, malonic, succinic, glutaric, fumaric, malic, tartaric, citric, ascorbic, maleic, hydroxymaleic, benzoic, hydroxy-benzoic, phenylacetic, cinnamic, salicyclic, 2-phenoxy-benzoic, and sulfonic acids such as p-toluenesulfonic acid, methane sulfonic acid and 2-hydroxyethane sulfonic acid. Such salts can exist in either a hydrated or substantially anhydrous form.

The expression "pharmaceutically acceptable basic addition salts" is intended to apply to any non-toxic organic or inorganic basic addition salts of a compound of Formula (I) or any of its intermediates. Illustrative bases which form suitable salts include alkali metal or alkaline-earth metal hydroxides such as sodium, potassium, calcium, magnesium, or barium hydroxides; ammonia, and aliphatic, cyclic, or aromatic organic amines such as methylamine, dimethylamine, trimethylamine, triethylamine, diethylamine, isopropyldiethylamine, pyridine and picoline.

As is appreciated by one of ordinary skill in the art the compounds of the Formula (I) may exist as stereoisomers. Any reference in this application to one of the compounds of the Formula (I) is meant to encompass either specific stereoisomers or a mixture of stereoisomers. The specific stereoisomers can be prepared by stereospecific synthesis or can be separated and recovered by techniques known in the art, such as chromatography, chromatography on chiral stationary phases, fractional recrystallization of addition salts formed by reagents used for that purpose, as described in *Enantiomers, Racemates, and Resolutions*, J. Jacques, A. Collet, and S. H. Wilen, Wiley (1981).

Examples of compounds encompassed by the present invention include:

[4S-[4α, 7α(R*), 12bβ]]-7-[(2-Thio-2-oxoindan)methylamino]- 1,2,3,4,6,7,8,12b-octahydro-6-oxopyrido[2,1-a][2]benzazepine-4-carboxylic acid, (S)-1-( 2-methylpropyl)-2-(thio)-ethylamine, disulfide;

[4S-[4α, 7α(R*), 12bβ]]-7-[(2-Thio-2-oxoindan)methylamino]-1,2,3,4,6,7,8,12b-octahydro-6-oxopyrido[2,1-a][2]benzazepine-4-carboxylic acid, (R)-1-(2-methylpropyl )-2-(thio)-ethylamine, disulfide;

[4S-[4α, 7α(R*), 12bβ]]-7-[(2-Thio-2-oxoindan)methylamino]-1,2,3,4,6,7,8,12b-octahydro-6-oxopyrido[2,1-a][2]benzazepine-4-carboxylic acid, pivaloyloxymethyl ester, (S)-1-(2-methylpropyl)-2-(thio)-ethylamine, disulfide;

[4S-[4α, 7α(R*), 12bβ]]-7-[(1-Thio-1-oxocyclopentane)methylamino]-1,2,3,4,6,7,8,12b-octahydro-6-oxopyrido[2, 1-a][2]benzazepine-4-carboxylic acid, (S)-1-(2-methylpropyl)-2-(thio)-ethylamine, disulfide;

[4S-[4α, 7α(R*), 12bβ]]-7-[(1-Thio-1-oxocyclopentane)methylamino]-1,2,3,4,6,7,8,12b-octahydro-6-oxopyrido[2, 1-a][2]benzazepine-4-carboxylic acid, (S)-1-(2-methylpropyl)-2-(thio)-ethylamine, disulfide;

[4S-[4α, 7α(R*), 12bβ]]-7-[(2-Thio-1-oxo-2-methyl)-2-propylamino]-1,2,3,4,6,7,8,12b-octahydro-6-oxopyrido [2,1-a][2]benzazepine-4-carboxylic acid, (S)-1-(2-methylpropyl)-2-(thio)-ethylamine, disulfide;

[4S-[4α, 7α(R*), 12bβ]]-7-[(2(2-Thio-ethyl-2-oxoindan)methylamino]-1,2,3,4,6,7,8,12b-octahydro-6-oxopyrido-6-oxopyrido[2,1-a][2]benzazepine-4-carboxylic acid, (S)-1-(2-methylpropyl)-2-(thio)-ethylamine, disulfide;

[4S-[4α, 7α(R*), 12bβ]]-7-[(2-Thio-methyl-2-oxoindan)methylamino]-1,2,3,4,6,7,8,12b-octahydro-6-oxopyrido-6-oxopyrido[2,1-a][2]benzazepine-4-carboxylic acid, (S)-1-(2-methylpropyl)-2-(thio)-ethylamine, disulfide;

[4S-[4α, 7α(R*), 12bβ]]-7-[(1-Thio-1-oxocyclohexane)methylamino]-1,2,3,4,6,7,8,12b-octahydro-6-oxopyrido-6-oxopyrido[2,1-a][2]benzazepine-4-carboxylic acid, (S)-1-(2-methylpropyl)-2-(thio)-ethylamine, disulfide;

[4S-[4α, 7α(R*), 12bβ]]-7-[(5-Thio-5-oxo-4,5,6-trihydro-cyclopental[c]furan)methylamino]-3,4,6,7,8,12b-hexahydro-6-oxo-1H-[1,4]-thiazino[3,4-a][2]benzazepine-4-carboxylic acid, (S)-1-(2-methylpropyl)-2-(thio)-ethylamine, disulfide;

[4S-[4α, 7α(R*), 12bβ]]-7-[(5-Thio-5-oxo-4,5,-dihydro-cyclopentimidazole)methylamino]-3,4,6,7,8,12b-hexahydro-6-oxo-1H-[1,4]-oxazino[3,4-a][2]benzazepine-4-carboxylic acid, (S)-1-(2-methylpropyl)-2-(thio)-ethylamine, disulfide;

[4S-[4α, 7α(R*), 12bβ]]-7-[(5-Thio-5-oxo-4,5,6-trihydro-cyclopental[c]thiophene)methylamino]-3,4,6,7,8,12b-hexahydro-6-oxo-1H-[1,4]-thiazino[3,4-a][2]benzazepine-4-carboxylic acid, (S)-1-(2-methylpropyl)-2-(thio)-ethylamine, disulfide;

[4S-[4α, 7α(R*), 12bβ]]-7-[(5-Thio-5-oxo-2,4,5,6-tetrahydro-cyclopental[c]pyrrole)methylamino]-3,4,6,7,8,12b-hexahydro-6-oxo-1H-[1,4]-azazino[3,4-a][2]benzazepine-4-carboxylic acid, (S)-1-(2-methylpropyl)-2-(thio)-ethylamine, disulfide;

[4S-[4α, 7α(R*), 12bβ]]-7-[(5-Thio-5-oxo-2,4,5,6-tetrahydro-cyclopental[c]pyrrole)methylamino]-3,4,6,7,8,12b-hexahydro-6-oxo-1H-[1,4]-azazino[3,4-a][2]benzazepine-4-carboxylic acid, (S)-1-(2-methylpropyl)-2-(thio)-ethylamine, disulfide;

[6α(R*), 11bβ]-6-[(5-Thio-5-oxo-2,4,5,6-tetrahydro-cyclopenta[c]pyrrole) methylamino]-1,2,3,4,5,6,7,11b-hexahydro-5-oxo-pyrrolo[2,1-a][2]benzazepine -3-(S)-carboxylic acid, (S)-1-(2-methylpropyl)-2-(thio)-ethylamine, disulfide;

[6α(R*), 11bβ]-6-[(5-Thio-5-oxo-2,4,5,6-tetrahydro-cyclopenta[c]pyrrole) methylamino]-1,2,3,4,5,6,7,11b-hexahydro-5-oxo-pyrrolo[2,1-a][2]benzazepine -3-(S)-carboxylic acid, (S)-1-(2-methylpropyl)-2-(thio)-ethylamine, disulfide;

[4S-[4α, 7α(R*), 12bβ]]-7-[(2-Thio-2-oxoindan)methylamino]-1,2,3,4,6,7,8,12b-octahydro-6-oxopyrido[2,1-a][2]benzazepine-4-carboxylic acid, L-cysteine ethyl ester, disulfide;

[4S-[4α, 7α(R*), 12bβ]]-7-[(2-Thio-2-oxoindan)methylamino]-1,2,3,4,6,7,8,12b-octahydro-6-oxopyrido[2,1-a][2]benzazepine-4-carboxylic acid, N-acetyl-L-cysteine, disulfide;

[4S-[4α, 7α(R*), 12bβ]]-7-[(2-Thio-2-oxoindan)methylamino]-1,2,3,4,6,7,8,12b-octahydro-6-oxopyrido[2,1-a][2]benzazepine-4-carboxylic acid, L-cysteine, disulfide;

[4S-[4α, 7α(R*), 12bβ]]-7-[(2-Thio-2-oxoindan)methylamino]-1,2,3,4,6,7,8,12b-octahydro-6-oxopyrido[2,1-a][2]benzazepine-4-carboxylic acid, benzylthio, disulfide;

[4S-[4α, 7α(R*), 12bβ]]-7-[(2-Thio-2-oxoindan)methylamino]-1,2,3,4,6,7,8,12b-octahydro-6-oxopyrido[2,1-a][2]benzazepine-4-carboxylic acid, ethylthio, disulfide;

[4S-[4α, 7α(R*), 12bβ]]-7-[(2-Thio-2-oxoindan)methylamino]-1,2,3,4,6,7,8,12b-octahydro-6-oxopyrido[2,1-a][2]benzazepine-4-carboxylic acid, 2-hydroxyethylthio, disulfide;

[4S-[4α, 7α(R*), 12bβ]]-7-[(2-Thio-2-oxoindan)methylamino]-1,2,3,4,6,7,8,12b-octahydro-6-oxopyrido[2,1-a][2]benzazepine-4-carboxylic acid, 2-pyridylmethyl, disulfide;

[4S-[4α, 7α(R*), 12bβ]]-7-[(2-Thio-2-oxoindan)methylamino]-1,2,3,4,6,7,8,12b-octahydro-6-oxopyrido[2,1-a][2]benzazepine-4-carboxylic acid, 2-thioacetic acid morpholine carboxamide, disulfide;

[4S-[4α, 7α(R*), 12bβ]]-7-[(2-Thio-2-oxoindan)methylamino]-1,2,3,4,6,7,8,12b-octahydro-6-oxopyrido[2,1-a][2]benzazepine-4-carboxylic acid, thiopyridine, disulfide;

A general synthetic procedure is set forth in Scheme A for preparing compounds of Formula (I). In Scheme A, all substituents unless otherwise indicated, are as previously defined. Starting materials, reagents, techniques, and procedures used in Scheme A are well known and appreciated by one of ordinary skill in the art.

SCHEME A

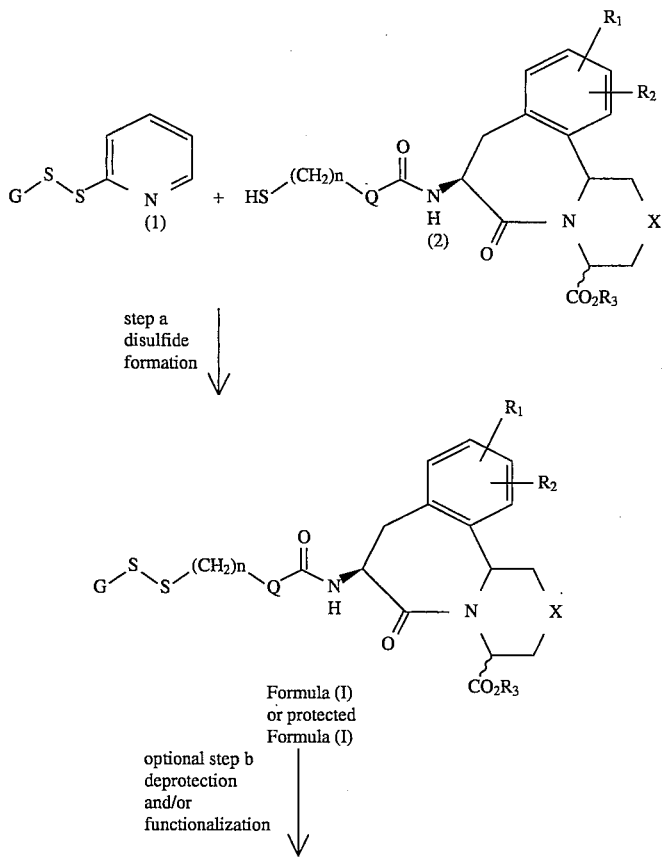

-continued
SCHEME A

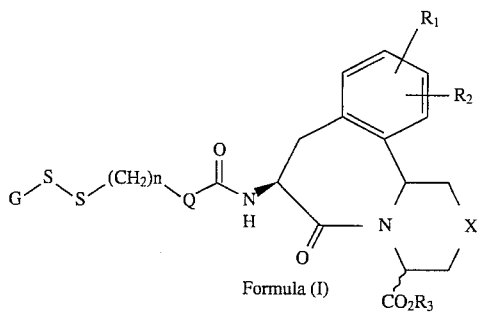

Formula (I)

The disulfide of structure (1) can be obtained by methods known in the art or by methods known analogously in the art, B. P. Roques et al. *J. Med. Chem.* 33, 2473–2481 (1992). The thiol of structure (2) are known in the art; European Patent Application No. 0 534 363, published Mar. 31, 1993; or are known analogously in the art.

In Scheme A, step a, an appropriate disulfide of structure (1) is contacted with an appropriate thiol of structure (2) to give a disulfide of Formula (I) or a protected disulfide of Formula (I). An appropriate disulfide of structure (1) is one in which G is as desired in the final product of Formula (I) or gives rise upon deprotection to G as is desired in the final product of Formula (I). An appropriate thiol of the structure (2) is one in which $R_1$, $R_2$, $R_3$, Q, X, and n are as desired in the final product of Formula (I) or give rise after deprotection and/or functionalization to $R_1$, $R_2$, $R_3$, Q, and X as desired in the final product of Formula (I).

For example, an appropriate disulfide of structure (1) is contacted with an appropriate thiol of structure (2). The reaction is carried out in a suitable solvent, such as ethanol, methanol, dichloromethane, or mixtures of ethanol or methanol and dichloromethane. The solvent is degassed by passing a stream of nitrogen gas through it for 15 minutes before the reaction is carried out. The reaction is carried out using from 1.0 to 4.0 molar equivalents of an appropriate compound of structure (1). The reaction is carried out at temperatures of from 0° C. to the refluxing temperature of the solvent, with a temperature of 10° C. to 30° C. being preferred. The reaction generally requires from 1 to 48 hours. The product can be isolated by techniques well known in the art, such as extraction, evaporation, and precipitation. The product can be purified by chromatography and recrystallization.

In Scheme A, optional step b, a protected disulfide of Formula (I) is deprotected and/or functionalized to give a disulfide of Formula (I).

The selection, use, and removal of protecting groups and the removal of protecting groups in a sequential manner utilizing suitable protecting groups such as those described in *Protecting Groups in Organic Synthesis* by T. Greene is well known and appreciated by those skilled in the art. The removal of protecting groups or the removal of protecting groups in a sequential manner as required gives disulfides of Formula (I).

A functionalization reaction includes the alkylation or acylation of amines and the formation of esters. These functionalizations can be carried out by methods which are well known in the art The following preparations and examples present typical syntheses as described in Scheme A. These preparations and examples are understood to be illustrative only and are not intended to limit the scope of the invention in any way. As used in the following preparations and examples, the following terms have the meanings indicated: "g" refers to grams, "mmol" refers to millimoles, "mL" refers to milliliters, "L" refers to liters, "° C." refers to degrees Celsius, "$R_f$" refers to retention factor, "mp" refers to melting point, "dec" refers to decomposition, "M" refers to molar, and "TLC" refers to thin layer chromatography.

PREPARATION 1 a) [4S-[4α, 7α(R*), 12bβ]]-7-[(2-Thioacetate-2-oxoindan)methylamino]-1,2,3,4,6,7,8,12b-octahydro-6-oxopyrido-[2,1-a][2]benzazepine-4-carboxylic acid Combine [4S-[4α, 7α(R*), 12bβ]]-7-[(2-thiol-2-oxoindan)methylamino]-1,2,3,4,6,7,8,12b-octahydro-6-oxopyrido[2,1-a][2]benzazepine-4-carboxylic acid (2.73 g, 6.07 mmol) and sulfuric acid (0.1 mL of a 10% solution in acetic acid). Add acetic anhydride (0.572 mL, 6.07 mmol) and stir for 2 hours. Dilute with ethyl ether, wash with water then saturated sodium hydrogen carbonate and brine. Dry (MgSO$_4$), evaporate the solvent in vacuo and purify by silica gel chromatography to give the title compound.

b) [4S-[4α, 7α(R*), 12bβ]]-7-[(1-Thioacetate-1-oxocyclopentane)methylamino]-1,2,3,4,6,7,8,12b-octahydro-6-oxopyrido[2,1-a][2]benzazepine-4-carboxylic acid Prepare in a manner similar to Preparation 1a using [4S-[4α,7α(R*), 12bβ]]-7-[(1-thio-1-oxocyclopentane)methylamino]-1,2,3,4,6,7,8,12b-octahydro-6-oxopyrido[2,1-a][2]benzazepine-4-carboxylic acid.

c) [4S-[4α, 7α(R*), 12bβ]]-7-[(1-Thioacetate-1-oxocyclopropane)methylamino)]-1,2,3,4,6,7,8,12b-octahydro-6-oxopyrido[2,1-a][2]benzazepine-4-carboxylic acid Prepare in a manner similar to Preparation 1a using [4S[4α, 7α(R*), 12bβ]]-7-[( 1-thio-1-oxocyclopropane)methylamino]-1,2,3,4,6,7,8,12b-octahydro-6-oxopyrido[2,1-a][2]benzazepine -4-carboxylic acid.

d) [4S-[4α, 7α(R*), 12bβ]]-7-[(2-Thioacetate-1-oxo-2-methyl)-2-propylamino]-1,2,3,4,6,7,8,12b-octahydro-6-oxopyrido[2,1-a][2]benzazepine-4-carboxylic acid Prepare in a manner similar to Preparation 1a using [4S-[4α,7α(R*), 12bβ]]-7-[(2-thio-1-oxo-2-methyl)-2-propylamino]-1,2,3,4,6,7,8,12b-octahydro-6-oxopyrido[2,1-a][2]benzazepine-4-carboxylic acid.

e) [4S-[4α, 7α(R*), 12bβ]]-7-[(2-(2-Thioacetate-ethyl)-2 -oxoindan)methylamino]-1,2,3,4,6,7,8,12b- octahydro-6-oxopyrido[2,1-a][2]benzazepine- 4-carboxylic acid Prepare in a manner similar to Preparation 1a using [4S-[4α, 7α(R*), 12bβ]]-7-[(2-(2-mercaptoethyl)-2-oxoindan)methylamino]-1,2,3,4,6,7,8,12b-octahydro-6-oxopyrido[2,1-a ][2]benzazepine-4-carboxylic acid.

f) [4S-[4α, 7α(R*), 12bβ]]-7-[(2-Thioacetate-methyl-2- oxoindan)methylamino]-1,2,3,4,6,7,8,12b- octahydro-6-oxopyrido[2,1- a][2]benzazepine-4-carboxylic acid Prepare in a manner similar to Preparation 1a using [4S-[4α, 7α(R*), 12bβ]]-7-[(2-mercaptomethyl-2-oxoindan)methylamino]-1,2,3,4,6,7,8,12b-octahydro-6-oxopyrido[2,1-a][2]benzazepine-4-carboxylic acid.

g) [4S-[4α, 7α(R*), 12bβ]]-7-[(1-Thioacetate-1- oxocyclohexane)methylamino]- 1,2,3,4,6,7,8,12b-octahydro-6- oxopyrido[2,1-a][2]benzazepine-4-carboxylic acid Prepare in a manner similar to Preparation 1a using [4S-[4α, 7α(R*), 12bβ]]-7-[(1-Thio-1-oxocyclohexane)methylamino]-1,2,3,4,6,7,8,12b-octahydro-6-oxopyrido[2,1-a][2]benzazepine-4-carboxylic acid.

h) [4S-[4α, 7α(R*), 12bβ]]-7-[(5-Thioacetate-5-oxo-4,5,6-trihydro -cyclopenta[c]furan)methylamino]-3,4,6,7,8,12b- hexahydro-6-oxo-1H-[1,4]-thiazino[3,4- a][2]benzazepine-4carboxylic acid Prepare in a manner similar to Preparation 1a using [4S-[4α, 7α(R*), 12bβ]]-7-[(5-thio-5-oxo-4,5,6-trihydro-cyclopenta[c]furan)methylamino]-3,4,6,7,8,12b-hexahydro-6-oxo-1H-[1,4]-thiazino[3,4-a][2]benzazepine -4-carboxylic acid.

i) [4S-[4α, 7α(R*), 12bβ]]-7-[(5-Thioacetate-5-oxo-4,5-dihydro -cyclopentimidazole)methylamino]-3,4,6,7,8,12b- hexahydro-6-oxo-1H-[1,4]-oxazino[3,4- a][2]benzazepine-4carboxylic acid Prepare in a manner similar to Preparation 1a using [4S-[4α, 7α(R*), 12bβ]]-7-[(5-thio-5-oxo-4,5-dihydro-cyclopentimidazole)methylamino]-3,4,6,7,8,12b-hexahydro-6-oxo-1H-[1,4]-oxazino[3,4-a][2]benzazepine-4-carboxylic acid.

j) [4S-[4α, 7α(R*), 12bβ]]-7-[(5-Thioacetate-5-oxo-4,5,6-trihydro -cyclopenta[c]thiophene)methylamino]-3,4,6,7,8,12b- hexahydro-6-oxo-1H-[1,4]- thiazino[3,4-a][2]benzazepine-4-carboxylic acid Prepare in a manner similar to Preparation 1a using [4S-[4α, 7α(R*), 12bβ]]-7-[(5-Thio-5-oxo-4,5,6-trihydro-cyclopenta[c]thiophene)methylamino]-3,4,6,7,8,12b-hexahydro-6-oxo-1H-[1,4]-thiazino[3,4-a][2]benzazepine-4-carboxylic acid.

k) [4S-[4α, 7α(R*), 12bβ]]-7-[(5-Thioacetate-5-oxo-2,4,5,6-tetrahydro -cyclopenta[c]pyrrole)methylamino]-3,4,6,7,8,12b- hexahydro-6-oxo-1H-[1,4]-azazino[3,4- a][2]benzazepine-4-carboxylic acid Prepare in a manner similar to Preparation 1a using [4S-[4α, 7α(R*), 12bβ]]-7-[(5-Thio-5-oxo-2,4,5,6-tetrahydro-cyclopenta[c]pyrrole)methylamino]-3,4,6,7,8,12b-hexahydro-6-oxo-1H-[1,4]-azazino[3,4-a][2]benzazepine -4-carboxylic acid.

l) [6α(R*), 11bβ]-6-[(S)-(5-Thioacetate-5-oxo-2,4,5,6- tetrahydro-cyclopenta[c]pyrrole) methylamino]- 1,2,3,5,6,7,11b-heptahydro-5-oxo- pyrrolo[2,1-a][2]benzazepine-3(S)-carboxylic acid Prepare in a manner similar to Preparation 1a using [6α(R*), 11bβ]-6-[(S)-(5-Thio-5-oxo-2,4,5,6-tetrahydro-cyclopenta [c]pyrrole) methylamino]-1,2,3,5,6,7,11b-heptahydro-5-oxo-pyrrolo[2,1-a][2]benzazepine-3(S) -carboxylic acid.

PREPARATION 2 a) [4S-[4α, 7α(R*), 12bβ]]-7-[(2-Thioacetate-2-oxoindan)methylamino]- 1,2,3,4,6,7,8,12b-octahydro-6-oxopyrido[2,1- a][2]benzazepine-4-carboxylic acid, diphenylmethyl ester Dissolve [4S-[4α, 7α(R*), 12bβ]]-7-[(2-Thioacetate-2-oxoindan)methylamino]-1,2,3,4,6,7,8,12b-octahydro-6-oxopyrido[2,1-a][2]benzazepine-4-carboxylic acid (0.28 mole) in methylene chloride (1.2 L) and dry over anhydrous MgSO$_4$ (60 g). Filter and wash with methylene chloride (3×200 mL). Evaporate in vacuo to a residue. Dissolve the residue in anhydrous dimethylformamide (860 mL) and place under nitrogen atmosphere. Add cesium carbonate (0.3 mole) in one portion. Stir for 45 minutes at ambient temperature. Add bromodiphenylmethane (0.67 mole). Stir the resulting mixture at ambient temperature for 18 hours. Quench the reaction with ethyl acetate (2.46 4 L) and water (630 mL). Separate the organic phase and wash with water (7×625 mL), ¼ saturated potassium hydrogen carbonate (625 mL), water (625 mL), and saturated sodium chloride (625 mL). Dry (MgSO$_4$), filter and evaporate in vacuo to yield a residue. Extract the combined aqueous washings with ethyl acetate (3×500 mL), wash with water (4×300 mL) and dry (MgSO$_4$). Filter and evaporate in vacuo to yield an additional amount of residue. Chromatograph the residues on silica gel to give the title compound.

b) [4S-[4α, 7α(R*), 12bβ]]-7-[(1-Thioacetate-1- oxocyclopentane)methylamino]-1,2,3,4,6,7,8,12b- octahydro-6-oxopyrido[2,1- a][2]benzazepine-4-carboxylic acid, diphenylmethyl ester Prepare in a manner similar to Preparation 2a using [4S-[4α, 7α(R*), 12bβ]]-7-[(1-Thioacetate-1-oxocyclopentane)methylamino]-1,2,3,4,6,7,8,12b-octahydro-6-oxopyrido[2,1-a][2]benzazepine-4-carboxylic acid.

c) [4S-[4α, 7α(R*), 12bβ]]-7-[(1-Thioacetate-1-oxocyclopropane)methylamino)]-1,2,3,4,6,7,8,12b-octahydro-6-oxopyrido[2,1-a][2]benzazepine-4-carboxylic acid diphenylmethyl ester Prepare in a manner similar to Preparation 2a using [4S-[4α, 7α(R*), 12bβ]]-7-[(1-Thioacetate-1-oxocyclopropane)methylamino]- 1,2,3,4,6,7,8,12b-octahydro-6-oxopyrido[2,1-a][2]benzazepine-4-carboxylic acid.

d) [4S-[4α, 7α(R*), 12bβ]]-7-[(2-Thioacetate-1-oxo-2-methyl)-2-propylamino]-1,2,3,4,6,7,8,12b-octahydro-6-oxopyrido[2,1-a][2]benzazepine-4-carboxylic acid, diphenylmethyl ester Prepare in a manner similar to Preparation 2a using [4S-[4α, 7α(R*), 12bβ]]-7-[(2-Thioacetate-1-oxo-2-methyl)-2-propylamino]-1,2,3,4,6,7,8,12b-octahydro-6-oxopyrido[2,1-a][2]benzazepine-4-carboxylic acid.

e) [4S-[4α, 7α(R*), 12bβ]]-7-[(2-Thioacetate-ethyl)-2-oxoindan)methylamino]-1,2,3,4,6,7,8,12b-octahydro-6-oxopyrido-6-oxopyrido[2,1-a][2]benzazepine-4-carboxylic acid, diphenylmethyl ester Prepare in a manner similar to Preparation 2a using [4S-[4α, 7α(R*), 12bβ]]-7-[(2-(2-Thioacetate-ethyl)-2-oxoindan)methylamino]-1,2,3,4,6,7,8,12b-octahydro-6-oxopyrido[2,1-a][2]benzazepine-4-carboxylic acid.

f) [4S-[4α, 7α(R*), 12bβ]]-7-[(2-Thioacetate-methyl-2-oxoindan)methylamino]-1,2,3,4,6,7,8,12b-octahydro-6-oxopyrido[2,1-a][2]benzazepine-4-carboxylic acid, diphenylmethyl ester Prepare in a manner similar to Preparation 2a using [4S-[4α, 7α(R*), 12bβ]]-7-[(2-Thioacetate-methyl-2-oxoindan)methylamino]-1,2,3,4,6,7,8,12b-octahydro-6-oxopyrido[2,1-a][2]benzazepine-4-carboxylic acid.

g) [4S-[4α, 7α(R*), 12bβ]]-7-[(1-Thioacetate-1-oxocyclohexane)methylamino]-1,2,3,4,6,7,8,12b-octahydro-6-oxopyrido[2,1-a][2]benzazepine-4-carboxylic acid, diphenylmethyl ester Prepare in a manner similar to Preparation 2a using [4S-[4α, 7α(R*), 12bβ]]-7-[(1-Thioacetate-1-oxocyclohexane)methylamino]-1,2,3,4,6,7,8,12b-octahydro-6-oxopyrido[2,1-a][2]benzazepine-4-carboxylic acid.

h) [4S-[4α, 7α(R*), 12bβ]]-7-[(5-Thioacetate-5-oxo-4,5,6-trihydro-cyclopenta[c]furan)methylamino]-3,4,6,7,8,12b-hexahydro-6-oxo-1H-[1,4]-thiazino[3,4-a][2]benzazepine-4-carboxylic acid, diphenylmethyl ester Prepare in a manner similar to Preparation 2a using [4S-[4α, 7α(R*), 12bβ]]-7-[(5-Thioacetate-5-oxo-4,5,6-trihydro-cyclopenta[c]furan)methylamino]-3,4,6,7,8,12b-hexahydro-6-oxo-1H-[1,4]-thiazino[3,4-a][2]benzazepine-4-carboxylic acid.

i) [4S-[4α, 7α(R*), 12bβ]]-7[(5-Thioacetate-5-oxo-4,5-dihydro-cyclopentimidazole)methylamino]-3,4,6,7,8,12b-hexahydro-6-oxo-1H-[1,4]-oxazino[3,4-a][2]benzazepine-4-carboxylic acid, diphenylmethyl ester Prepare in a manner similar to Preparation 2a using [4S-[4α, 7α(R*), 12bβ]]-7-[(5-Thioacetate-5-oxo-4,5-dihydro-cyclopentimidazole)methylamino]-3,4,6,7,8,12b-hexahydro-6-oxo-1H-[1,4]-oxazino[3,4-a][2]benzazepine-4-carboxylic acid.

j) [4S-[4α, 7α(R*), 12bβ]]-7-[(5-Thioacetate-5-oxo-4,5,6-trihydro-cyclopenta[c]thiophene)methylamino]-3,4,6,7,8,12b-hexanhydro-6-oxo-1H-[1,4]-thiazino[3,4-a][2]benzazepine-4-carboxyiic acid, diphenylmethyl ester Prepare in a manner similar to Preparation 2a using [4S-[4α, 7α(R*), 12bβ]]-7-[(5-Thioacetate-5-oxo-4,5,6-trihydro-cyclopenta[c]thiophene)methylamino]-3,4,6,7,8,12b-hexahydro-6-oxo-1H-[1,4]-thiazino[3,4-a][2]benzazepine-4-carboxylic acid.

k) [4S-[α, 7α(R*), 12bβ]]-7-[(5-Thioacetate-5-oxo-2,4,5,6-tetrahydro-cyclopenta[c]pyrrole)methylamino]-3,4,6,7,8,12b-hexahydro-6-oxo-1H-[1,4]-azazino[3,4-a][2]benzazepine-4carboxylic acid, diphenylmethyl ester Prepare in a manner similar to Preparation 2a using [4S-[4α, 7α(R*), 12bβ]]-7-[(5-Thioacetate-5-oxo-2,4,5,6-tetrahydro -cyclopenta[c]pyrrole)methylamino]-3,4,6,7,8,12b-hexahydro-6-oxo-1H-[1,4]-azazino[3,4-a][2]benzazepine-4-carboxylic acid.

l) [6α(R*), 11bβ]-6-[(S)-(5-Thioacetate-5-oxo-2,4,5,6-tetrahydro-cyclopenta[c]pyrrole)methylamino]-1,2,3,5,6,7,11b-heptahydro-5-oxo-pyrrolo[2,1-a][2]benzazepine-3(S)-carboxylic acid, diphenylmethyl ester Prepare in a manner similar to Preparation 2a using [6α(R*), 11bβ]-6-[(S)-(5-Thioacetate-5-oxo-2,4,5,6-tetrahydro -cyclopenta[c]pyrrole)methylamino]-1,2,3,5,6,7,11b-heptahydro-5-oxo-pyrrolo[2,1-a][2]benzazepine-3(S)-carboxylic acid.

PREPARATION 3 a) [4S-[4α, 7α(R*), 12bβ]]-7-[(2-Thio-2-oxoindan)methylamino]-1,2,3,4,6,7,8,12b-octahydro-6-oxopyrido[2,1-a][2]benzazepine-4-carboxylic acid diphenylmethyl ester Stir [4S-[4α, 7α(R*), 12bβ]]-7-[(2-Thioacetate-2-oxoindan)methylamino]-1,2,3,4,6,7,8,12b-octahydro-6-oxopyrido[2,1-a][2]benzazepine-4-carboxylic acid, diphenylmethyl ester (4 mmol) and saturated methanolic ammonia (20 mL) at ambient temperature until hydrolysis is complete. Evaporate the solvent in vacuo a and purify by silica gel chromatography to give the title compound.

b) [4S-[4α, 7α(R*), 12bβ]]-7-[(1-Thio-1-oxocyclopentane)methylamino]-1,2,3,4,6,7,8,12b-octahydro-6-oxopyrido[2,1-a][2]benzazepine-4-carboxylic acid, diphenylmethyl ester Prepare in a manner similar to Preparation 3a using [4S-[4α, 7α(R*), 12bβ]]-7-[(1-Thioacetate-1-oxocyclopentane)methylamino]-1,2,3,4,6,7,8,12b-octahydro-6-oxopyrido[2,1-a][2]benzazepine-4-carboxylic acid, diphenyl ester.

c) [4S-[4α, 7α(R*), 12bβ]]-7-[(1-Thio-1-oxocyclopropane)methylamino]-1,2,3,4,6,7,8,12b-octahydro-6-oxopyrido[2,1-a][2]benzazepine-4-carboxylic acid, diphenylmethyl ester Prepare in a manner similar to Preparation 3a using [4S-[4α, 7α(R*), 12bβ]]-7-[(1-Thioacetate-1-oxocyclopropane)methylamino]-1,2,3,4,6,7,8,12b-octahydro-6-oxopyrido[2,1-a][2]benzazepine-4-carboxylic acid, diphenylmethyl ester.

d) [4S-[4α, 7α(R*), 12bβ]]-7-[(2-Thio-1-oxo-2-methyl)-2-propylamino]-1,2,3,4,6,7,8,12b-octahydro-6-oxopyrido[2,1a-][2]benzazepine-4-carboxylic acid, diphenylmethyl ester Prepare in a manner similar to Preparation 3a using [4S-[4α, 7α(R*), 12bβ]]-7-[(2-Thioacetate-1-oxo-2-methyl)-2-propylamino]-1,2,3,4,6,7,8,12b-octahydro-6-oxopyrido[2,1-a][2]benzazepine-4-carboxylic acid, diphenylmethyl ester.

e) [4S-[4α, 7α(R*), 12bβ]]-7-[(2-(2-Thio-ethyl)-2-oxoindan)methylamino]-1,2,3,4,6,7,8,12b-octahydro-6-oxopyrido[2,1-a][2]benezazepine-4-carboxylic acid, diphenylmethyl ester Prepare in a manner similar to Preparation 3a using [4S-[4α, 7α(R*), 12bβ]]-7-[(2-(2-Thioacetate-ethyl)-2-oxoindan)methylamino]-1,2,3,4,6,7,8,12b-octahydro-6-oxopyrido[2,1-a][2]benzazepine-4-carboxylic acid, diphenylmethyl ester.

f) [4S-[4α, 7α(R*), 12bβ]]-7-[(2-Thio-methyl-2-oxoindan)methylamino]-1,2,3,4,6,7,8,12b-octahydro-6-oxopyrido[2,1-a][2]benzazepine-4-carboxylic acid, diphenylmethyl ester Prepare in a manner similar to Preparation 3a using [4S-[4α, 7α(R*), 12bβ]]-7-[(2-Thioacetate-methyl-2-oxoindan)methylamino]-1,2,3,4,6,7,8,12b-octahydro-6-oxopyrido[2,1-a][2]benzazepine-4-carboxylic acid, diphenylmethyl ester.

g) [4S-[4α, 7α(R*), 12bβ]]-7-[(1-Thio-1-oxocyclohexane)methylamino]-1,2,3,4,6,7,8,12b-octahydro-6-oxopyrido[2,1-a][2]benzazepine-4-carboxylic acid, diphenylmethyl ester Prepare in a manner similar to Preparation 3a using [4S-[4α, 7α(R*), 12bβ]]-7-[(1-Thioacetate-1-oxocyclohexane)methylamino]-1,2,3,4,6,7,8,12b-octahydro-6-oxopyrido[2,1-a][2]benzazepine-4-carboxylic acid, diphenylmethyl ester.

h) [4S-[4α, 7α(R*), 12bβ]]-7-[(5-Thio-5-oxo-4,5,6-trihydro-cyclopenta[c]furan)methylamino]-3,4,6,7,8,12b-hexahydro-6-oxo-1H-[1,4]-thiazino[3,4-a][2]benzazepine-4-carboxylic acid, diphenylmethyl ester Prepare in a manner similar to Preparation 3a using [4S-[4α, 7α(R*), 12bβ]]-7-[(5-Thioacetate-5-oxo-4,5,6-trihydro-cyclopenta[c]furan)methylamino]-3,4,6,7,8,12b-hexahydro-6-oxo-1H-[1,4]-thiazino[3,4-a][2]benzazepine-4-carboxylic acid, diphenylmethyl ester.

i) [4S-[4α, 7α(R*), 12bβ]]-7-[(5-Thio-5-oxo-4,5-dihydro-cyclopentimidazole)methylamino]-3,4,6,7,8,12b-hexahydro-6-oxo-1H-[1,4]-oxazino[3,4-a][2]benzazepine-4-carboxylic acid, diphenylmethyl ester Prepare in a manner similar to Preparation 3a using [4S-[4α, 7α(R*), 12bβ]]-7-[(5-Thioacetate-5-oxo-4,5-dihydro-cyclopentimidazole)methylamino]-3,4,6,7,8,12b-hexahydro-6-oxo-1H-[1,4]-oxazino[3,4-a][2]benzazepine-4-carboxylic acid, diphenylmethyl ester.

j) [4S-[4α, 7α(R*), 12bβ]]-7-[(5-Thio-5-oxo-4,5,6-trihydro-cyclopenta[c]thiophene)methylamino]-3,4,6,7,8,12b-hexahydro-6-oxo-1H-[1,4]-thiazino[3,4-a][2]benzazepine-4-carboxylic acid, diphenylmethyl ester Prepare in a manner similar to Preparation 3a using [4s[4α, 7α(R*), 12bβ]]-7-[(5-Thioacetate-5-oxo-4,5,6-trihydro-cyclopenta[c]thiophene)methylamino]-3,4,6,7,8,12b-hexahydro-6-oxo-1H-[1,4]-thiazino[3,4-a][2]benzazepine-4-carboxylic acid, diphenylmethyl ester.

k) [4S-[4α, 7α(R*), 12bβ]]-7-[(5-Thio-5-oxo-2,4,5,6-tetrahydro-cyclopenta[c]pyrrole)methylamino]-3,4,6,7,8,12b-hexahydro-6-oxo-1H-[1,4]-azazino[3,4-a][2]benzazepine-4-carboxylic acid, diphenylmethyl ester Prepare in a manner similar to Preparation 3a using [4S-[4α, 7α(R*), 12bβ]]-7-[(5-Thioacetate-5-oxo-2,4,5,6-tetrahydro-cyclopenta[c]pyrrole)methylamino]-3,4,6,7,8,12b-hexahydro-6-oxo-1H-[1,4]-azazino[3,4-a][2]benzazepine-4-carboxylic acid, diphenylmethyl ester.

l) [6α(R*), 11bβ]-6-[(S)-(5-Thio-5-oxo-2,4,5,6-tetrahydro-cyclopenta[c]pyrrole)methylamino]-1,2,3,4,5,6,7,11b-heptahydro-5-oxo-pyrrolo[2,1-a][2,1-a]benzazepine-3(S)-carboxylic acid, diphenylmethyl ester Prepare in a manner similar to Preparation 3a using [6α(R*), 11bβ]-6-[(S)-(5-Thioacetate-5-oxo-2,4,5,6-tetrahydro-cyclopenta[c]pyrrole)methylamino]-1,2,3,5,6,7,11b-heptahydro-5-oxo-pyrrolo[2,1-a][2]benzazepine-3(S)-carboxylic acid, diphenylmethyl ester.

EXAMPLE 1

[4S-[4α, 7α(R*),
12bβ]]-7-[(2-Thio-2-oxoindan)methylamino]-
1,2,3,4,6,7,8,12b-octahydro-6-oxopyrido[2,1-
a][2]benzazepine-4-carboxylic acid, diphenylmethyl
ester, (S)-N-(t
butoxycarbonyl)-1-(2-methylpropyl)-2-
(thio)-ethylamine, disulfide;

Scheme A, step a:

Combine [4S-[4α, 7α(R*), 12bβ]]-7-[(2-thio-2-oxoindan)methylamino]-1,2,3,4,6,7,8,12b-octahydro-6-oxopyrido[2,1-a][2]benzazepine-4-carboxylic acid, diphenylmethyl ester (2 mmol) and (S)-N-(t-butoxycarbonyl)-1-(2-methylpropyl)-2-(thio)-ethylamine, 2-thiopyridine, disulfide (2.2 mmol) in degassed ethanol (7 mL). Stir for 18 hours. Evaporate in vacuo. Chromatograph on silica gel to give the title compound.

EXAMPLE 2

[4S-[4α, 7α(R*),
12bβ]]-7-[(2-Thio-2-oxoindan)methylamino]-
1,2,3,4,6,7,8,12,b-octahydro-6-
oxopyrido[2,1-a][2]benzazepine-4-carboxylic acid,
pivaloyloxymethyl ester,
(S)-N-(t-butoxycarbonyl)-1-(2-methylpropyl)-2-(thio)-
ethylamine, disulfide;

Scheme A, step a:

Prepare in a manner similar to Example 1 using 4S-[4α, 7α(R*), 12bβ]]-7-[(2-thio-2-oxoindan)methylamino]-1,2,3,4,6,7,8,12b-octahydro-6-oxopyrido[2,1-a][2]benzazepine-4-carboxylic acid, pivaloyloxymethyl ester.

EXAMPLE 3

[4S-[4α, 7α(R*),
12bβ]]-7-[(1-Thio-1-oxocyclopentane)methylamino]-
1,2,3,46,7,8,12b-octahydro-6-
oxopyrido[2,1-a][2]benzazepine-
4-carboxylic acid, diphenylmethyl ester,
(S)-N-(t-butoxycarbonyl)-1-(2-methylpropyl)-2-(thio)-
ethylamine, disulfide;

Scheme A, step a:

Prepare in a manner similar to Example 1 using [4S-[4α, 7α(R*), 12bβ]]-7-[(1-thio-1-oxocyclopentane)methylamino]-1,2,3,4,6,7,8,12b-octahydro-6-oxopyrido[2,1-a][2]benzazepine-4-carboxylic acid, diphenylmethyl ester.

EXAMPLE 4

[4S-[4α, 7α(R*),
12bβ]]-7-[(1-Thio-1-oxocyclopropane)methylamino]-
1,2,3,4,6,7,8,12b-octahydro-6-oxopyrido[2,1-
a][2]benzazepine-4-carboxylic acid, diphenylmethyl
ester,
(S)-N-(t-butoxycarbonyl)-1-(2-methylpropyl)-2-
(thio)-ethylamine, disulfide;

Scheme A, step a:

Prepare in a manner similar to Example 1 using [4S-[4α, 7α(R*), 12bβ]]-7-[(1-Thio-1-oxocyclopropane)methylamino]-1,2,3,4,6,7,8,12b-octahydro-6-oxopyrido[2,1-a][2]benzazepine-4-carboxylic acid, diphenylmethyl ester.

EXAMPLE 5

[4S-[4α, 7α(R*),
12bβ]]-7-[(2-Thio-1-oxo-2-methyl)-2-propylamino]-
1,2,3,4,6,7,8,12b-octahydro-6-oxopyrido[2,1-
a][2]benzazepine-4-carboxylic acid, diphenylmethyl
ester,
(S)-N-(t-butoxycarbonyl)-1-(2-methylpropyl)-2-(thio)-
ethylamine, disulfide;

Scheme A, step a:

Prepare in a manner similar to Example 1 using [4S-[4α, 7α(R*), 12bβ]]-7-[(2-thio-1-oxo-2-methyl)-2-propylamino]-1,2,3,4,6,7,8,12b-octahydro-6-oxopyrido[2,1-a][2]benzazepine-4-carboxylic acid, diphenylmethyl ester.

EXAMPLE 6

[4S-[4α, 7α(R*),
12bβ]]-7-[(2-(2-Thio-ethyl)-2-oxoindan)methylamino]-
1,2,3,4,6,7,8,12b-octahydro-6-oxopyrido[2,1-
a][2]benzazepine-4-carboxylic acid, diphenylmethyl
ester,
(S)-N-(t-butoxycarbonyl)-1-(2-methylpropyl)-2-(thio)-
ethylamine, disulfide;

Scheme A, step a:

Prepare in a manner similar to Example 1 using [4S-[4α, 7α(R*), 12bβ]]-7-[(2-(2-Thio-ethyl)-2-oxoindan)methylamino]-1,2,3,4,6,7,8,12b-octahydro-6-oxopyrido[2,1-a][2]benzazepine-4-carboxylic acid, diphenylmethyl ester.

EXAMPLE 7

[4S-[4α, 7α(R*),
12bβ]]-7-[(2-Thio-methyl-2-oxoindan)methylamino]-
1,2,3,4,6,7,8,12b-octahydro-6-oxopyrido[2,1-
a ][2]benzazepine-4-carboxylic acid,
diphenylmethyl ester,
(S)-N-(t-butoxycarbonyl)-1-(2-methylpropyl)-2-(thio)-
ethylamine, disulfide;

Scheme A, step a:

Prepare in a manner similar to Example 1 using [4S-[4α, 7α(R*), 12bβ]]-7-[(2-Thio-methyl-2-oxoindan)methylamino]-1,2,3,4,6,7,8,12b-octahydro-6-oxopyrido[2,1-a][2]benzazepine-4-carboxylic acid, diphenylmethyl ester.

EXAMPLE 8

[4S-[4α, 7α(R*),
12bβ]]-7-[(1-Thio-1-oxocyclohexane)methylamino]-
1,2,3,4,6,7,8,12b-octahydro-6-oxopyrido[2,1-
a][2]benzazepine-4-carboxylic acid, diphenylmethyl
ester,
(S)-N-(t-butoxycarbonyl)-1-(2-methylpropyl)-2-(thio)-
ethylamine, disulfide;

Scheme A, step a:

Prepare in a manner similar to Example 1 using [4S-[4α, 7α(R*), 12bβ]]-7-[(1-Thio-1-oxocyclohexane)methylamino]-1,2,3,4,6,7,8,12b-octahydro-6-oxopyrido[2,1-a][2]benzazepine-4-carboxylic acid, diphenylmethyl ester.

EXAMPLE 9

[4S-[4α, 7α(R*) 12bβ]]-7-[(5-Thio-5-oxo-4,5,6-trihydro-cyclopenta[c]furan)methylamino]-3,4,6,7,8,12b-hexahydro-6-oxo-1H-[1,4]-thiazino[3,4-a][2]benzazepine-4-carboxylic acid, diphenylmethyl ester, (S)-N-(t-butoxycarbonyl)-1-(2-methylpropyl)-2-(thio)-ethylamine, disulfide;

Scheme A step a:

Prepare in a manner similar to Example 1 using [4S-[4α, 7α(R*), 12bβ]]-7-[(5-thio-5-oxo-4,5,6-trihydro-cyclopenta[c]furan)methylamino]-3,4,6,7,8,12b-hexahydro-6-oxo-1H-[1,4]-thiazino[3,4-a ][2 ]benzazepine-4-carboxylic acid, diphenylmethyl ester.

EXAMPLE 10

[4S-[4α, 7α(R*), 12bβ]]-7-[(5-Thio-5-oxo-4,5-dihydro-cyclopentimidazole)methylamino]-3,4,6,7,8,12b-hexahydro-6-oxo-1H-[1,4 ]-oxazino[3,4-a ][2]benzazepine-4-carboxylic acid, diphenylmethyl ester, (S)-N-(t-butoxycarbonyl)-1-(2-methylpropyl)-2-(thio)-ethylamine, disulfide;

Scheme A, step a:

Prepare in a manner similar to Example 1 using [4S-[4α, 7α(R*), 12bβ]]-7-[(5-thio-5-oxo-4,5-dihydro-cyclopentimidazole)methylamino]-3,4,6,7,8,12b-hexahydro-6-oxo-1H-[1,4]-oxazino[3,4-a][2]benzazepine-4-carboxylic acid, diphenylmethyl ester.

EXAMPLE 1

[4S-[4α, 7α(R*), 12bβ]]-7-[(5-Thio-5-oxo-4,5,6-trihydro-cyclopenta[c]thiophene)methylamino]-3,4,6,7,8,12b-hexahydro-6-oxo-1H-[1,4]-thiazino[3,4-a][2]benzazepine-4-carboxylic acid, diphenylmethyl ester, (S)-N-(t-butoxycarbonyl)-1-(2-methylpropyl)-2-(thio)-ethylamine, disulfide;

Scheme A, step a:

Prepare in a manner similar to Example 1 using [4S-[4α, 7α(R*), 12bβ]]-7-[(5-Thio-5-oxo-4,5,6-trihydro-cyclopenta[c]thiophene)methylamino]-3,4,6,7,8,12b-hexahydro-6-oxo-1H-[1,4]-thiazino[3,4-a][2]benzazepine-4-carboxylic acid, diphenylmethyl ester.

EXAMPLE 12

[4S-[4α, 7α(R*), 12bβ]]-7-[(5-Thio-5-oxo-2,4,5,6-tetrahydro-cyclopenta[c]pyrrole)methylamino]-3,4,6,7,8,12b-hexahydro-6-oxo-1H-[1,4]-azazino[3,4-a][2]benzazepine-4-carboxylic acid diphenylmethyl ester, (S)-N-(t-butoxycarbonyl)-1-(2-methylpropyl)-2-(thio)-ethylamine, disulfide;

Scheme. A, step a:

Prepare in a manner similar to Example 1 using [4S-[4α, 7α(R*), 12bβ]]-7-[(5-Thio-5-oxo-2,4,5,6-tetrahydro-cyclopenta [c]pyrrole)methylamino]-3,4,6,7,8,12b-hexahydro-6-oxo-1H-[1,4]-azazino[3,4-a][2]benzazepine-4-carboxylic acid, diphenylmethyl ester.

EXAMPLE 13

[6α(R*), 11bβ]-6-[(S)-(5-Thio-5-oxo-2,4,5,6-tetrahydro-cyclopenta[c]pyrrole)methylamino]-1,2,3,5,6,7,11b-heptahydro-5-oxo-pyrrolo[-2,1-a][2]benzazepine-3(S)-carboxylic acid, diphenylmethyl ester, (S)-N-(t-butoxycarbonyl)-1-(2-methylpropyl)-2-(thio)-ethylamine, disulfide Scheme A, step a:

Prepare in a manner similar to Example 1 using [6α(R*), 11bβ]-6-[(S)-(5-Thio-5-oxo-2,4,5,6-tetrahydro-cyclopenta[c]pyrrole)methylamino]-1,2,3,5,6,7,11b-heptahydro-5-oxo-pyrrolo[2,1-a][2]benzazepine-3(S)-carboxylic acid, diphenylmethyl ester.

EXAMPLE 14

[4S-[4α, 7α(R*), 12bβ]]-7-[(2-Thio-2-oxoindan)methylamino]-1,2,3,4,6,7,8,12b-octahydro-6-oxopyrido[2,1-a][2]benzazepine-4-carboxylic acid, (S)-1-(2-methylpropyl)-2-(thio)-ethylamine, disulfide trifluoroacetic acid salt;

Scheme A, optional step b:

Combine [4S-[4α, 7α(R*), 12bβ]]-7-[(2-Thio-2-oxoindan)methylamino-]-1,2,3,4,6,7,8,12b-octahydro-6-pxpomdam)methylamino]2,1-a][2]benzazepine-4-carboxylic acid, diphenylmethyl ester, (S)-N-(t-butoxycarbonyl)-1-(2-methylpropyl)-2-(thio)-ethylamine, disulfide (1 mmol), anisole (10 mmol), and trifluoroacetic acid (1 mL in dichloromethane (5 mL). Stir for 3 hours and evaporate in vacuo. Repeatedly, add carbon tetrachloride and evaporate in vacuo to remove residual trifluoroacetic acid. Evaporation in vacuo from hexane/dichloromethane gives the title compound as a solid.

EXAMPLE 15

4S-[4α, 7α(R*), 12bβ]]-7-[(2-Thio-2-oxoindan)methylamino]-1,2,3,4,6,7,8,12b-octahydro-6-oxopyridol[2,1-a][2 ]benzazepine-4-carboxylic acid, pivaloyloxymethyl ester, (S)-1-(2-methylpropyl)-2-(thio)-ethylamine, disulfide trifluoroacetic acid salt;

Scheme A, optional step b:

Prepare in a manner similar to Example 14 using [4S-[4α, 7α(R*), 12bβ]]-7-[(2-Thio-2-oxoindan)methylamino]-1,2,3,4,6,7,8,12b-octahydro-6-oxopyrido[2,1-a][2]benzazepine-4-carboxylic acid, pivaloyloxymethyl ester, (S)-N-(t-butoxycarbonyl)-1-(2-methylpropyl)-2-(thio)-ethylamine, disulfide.

EXAMPLE 16

[4S-[4α, 7α(R*),
12bβ]],7-[(1-Thio-1-oxocyclopentane)methylamino]-
1,2,3,4,6,7,8,12b-octahydro-6-oxopyrido[2,1-
a][2,1]benzazepine-4-carboxylic acid,
(S)-1-(2-methylpropyl)-2-(thio)-ethylamine,
disulfide trifluoroacetic acid salt;

Scheme A, optional step b:

Prepare in a manner similar to Example 14 using [4S-[4α, 7α(R*), 12bβ]]-7-[(1-Thio-1-oxocyclopentane)methylamino]-1,2,3,4,6,7,8,12b-octahydro-6-oxopyrido[2,1-a][2]benzazepine-4-carboxylic acid, diphenylmethyl ester, (S)-N-(t-butoxycarbonyl)-1-(2-methylpropyl)-2-(thio)-ethylamine, disulfide.

EXAMPLE 17

[4S-[4α, 7α(R*),
12bβ]]-7-[(1-Thio-1-oxocyclopropane)methylamino]-
1,2,3,4,6,7,8,12b-octahydro-6-oxopyrido[2,1-
a][2]benzazepine-4-carboxylic acid, diphenylmethyl
ester, (S)-1-(2-methylpropyl)-2-(thio)-ethylamine,
disulfide trifluoroacetic acid salt;

Scheme A, optional step b:

Prepare in a manner similar to Example 14 using [4S-[4α, 7α(R*), 12bβ]]-7-[(1-Thio-1-oxocyclopropane)methylamino]-1,2,3,4,6,7,8,12b-octahydro-6-oxopyrido[2,1-a][2]benzazepine-4-carboxylic acid, diphenylmethyl ester, (S)-N-(t-butoxycarbonyl)-1-(2-methylpropyl)-2-(thio)-ethylamine, disulfide.

EXAMPLE 18

[4S-[4α, 7α(R*), 12bβ]]-7-[(2-Thio-1-oxo-
2-methyl)-2-propylamino]-1,2,3,4,6,7,8,12b-
octahydro-6-oxopyrido[2,1-a][2]benzazepine-4-
carboxylic acid,
(S)-1-(2-methylpropyl)-2-(thio)-ethylamine,
disulfide trifluoroacetic acid salt;

Scheme A, optional step b:

Prepare in a manner similar to Example 14 using [4S-[4α, 7α(R*), 12bβ]]-7-[(2-Thio-1-oxo-2-methyl)-2-propylamino]-1,2,3,4,6,7,8,12b-octahydro-6-oxopyrido[2,1-a][2]benzazepine-4-carboxylic acid, diphenylmethyl ester, (S)-N-(t-butoxycarbonyl)-1-(2-methylpropyl)-2-(thio)-ethylamine, disulfide.

EXAMPLE 19

[4S-[4α, 7α(R*), 12bβ]]-7-[(2-(2-Thio-ethyl)-
2-oxoindan)methylamino]-1,2,3,4,6,7,8,12b-octahydro-
6-oxopyrido[2,1-a][2]benzazepine-4-
carboxylic acid,
(S)-1-(2-methylpropyl)-2-(thio)-ethylamine,
disulfide trifluoroacetic acid salt;

Scheme A, optional step b:

Prepare in a manner similar to Example 14 using [4S-[4α, 7α(R*), 12bβ]]-7-[(2-(2-Thio-ethyl)-2-oxoindan)methylamino]-1,2,3,4,6,7,8,12b-octahydro-6-oxopyrido[2,1-a][2]benzazepine-4-carboxylic acid, diphenylmethyl ester, (S)-N-(t-butoxycarbonyl)-1-(2-methylpropyl)-2-(thio)-ethylamine, disulfide.

EXAMPLE 20

[4S-[4α, 7α(R*),
12bβ]]-7-[(2-Thio-methyl-2-oxoindan)methylamino]-
1,2,3,4,6,7,8,12b-octahydro-6-oxopyrido[2,1-
a][2]benzazepine-4-carboxylic acid,
(S)-1-(2-methylpropyl)-2-(thio)-ethylamine,
disulfide trifluoroacetic acid salt;

Scheme A, optional step b:

Prepare in a manner similar to Example 14 using [4S-[4α, 7α(R*), 12bβ]]-7-[(2-Thio-methyl-2-oxoindan)methylamino]-1,2,3,4,6,7,8,12b-octahydro-6-oxopyrido[2,1-a][2]benzazepine-4-carboxylic acid, diphenylmethyl ester, (S)-N-(t-butoxycarbonyl)-1-(2-methylpropyl)-2-(thio)-ethylamine, disulfide.

EXAMPLE 21

[4S-[4α, 7α(R*),
12bβ]]-7-[(1-Thio-1-oxocyclohexane)
methylamino]-1,2,3,4,5,6,7,8,12b-octahydro-6-
oxopyrido[2,1-a][2]benzazepine-4-
carboxylic acid,
(S)-1-(2-methylpropyl)-2-(thio)-ethylamine,
disulfide trifluoroacetic acid salt;

Scheme A, optional step b:

Prepare in a manner similar to Example 14 using [4S-[4α, 7α(R*), 12bβ]]-7-[(1-Thio-1-oxocyclohexane)methylamino]-1,2,3,4,6,7,8,12b-octahydro-6-oxopyrido[2,1-a][2]benzazepine-4-carboxylic acid, diphenylmethyl ester, (S)-N-(t-butoxycarbonyl)-1-(2-methylpropyl)-2-(thio)-ethylamine.

EXAMPLE 22

[4S-[4α, 7α(R*),
12bβ]]-7-[(5-Thio-5-oxo-4,5,6-trihydro-
cyclopenta[c]furan)methylamino]-3,4,6,7,8,12b,-
hexahydro-6-oxo-1H-[1,4]-thiazino[3,4-
a][2]benzazepine-4-carboxylic acid,
(S)-1-(2-methylpropyl)-2-(thio)-ethylamine,
disulfide trifluoroacetic acid salt;

Scheme A, optional step b:

Prepare in a manner similar to Example 14 using [4S-[4α, 7α(R*), 12bβ]]-7-[(5-Thio-5-oxo-4,5,6-trihydro-cyclopenta[c]furan)methylamino]-3,4,6,7,8,12b-hexahydro-6-oxo-1H-[1,4]-thiazino[3,4-a][2]benzazepine-4-carboxylic acid, diphenylmethyl ester, (S)-N-(t-butoxycarbonyl)-1-(2-methylpropyl)- 2-(thio)-ethylamine, disulfide.

EXAMPLE 23

[4S,[4α, 7α(R*),
12bβ]]-7-[(5-Thio-5-oxo-4,5-dihydro-
cyclopentimidazole)
methylamino]-3,4,6,7,8,12b-hexahydro-6-oxo-
1H-[1,4]-oxazino[3,4-a][2]benzazepine-4-carboxylic
acid, (S)-1-(2-methylpropyl)-2-(thio)-ethylamine,
disulfide trifluoroacetic acid salt;

Scheme A, optional step b:

Prepare in a manner similar to Example 14 using [4S-[4α, 7α(R*), 12bβ]]-7-[(5-Thio-5-oxo-4,5-dihydro-cyclopentimidazole)methylamino]-3,4,6,7,8,12b-hexahydro-6-oxo-1H-[1,4]-oxazino[3,4-a][2]benzazepine-4-carboxylic acid, diphenylmethyl ester, (S)-N-(t-butoxycarbonyl)-1-(2-methylpropyl)- 2-(thio)-ethylamine, disulfide.

EXAMPLE 24

[4S-[4α, 7α(R*), 12bβ]]-7-[(5-Thio-5-oxo-4,5,6-trihydro-cyclopenta[c]thiophene)methylamino]-3,4,6,7,8,12b-hexahydro-6-oxo-1H-[1,4]-thiazino[3,4-a][2]benzazepine-4-carboxylic acid, (S)-1-(2-methylpropyl)-2-(thio)-ethylamine, disulfide trifluoroacetic acid salt;

Scheme A, optional step b:

Prepare in a manner similar to Example 14 using [4S-[4α, 7α(R*), 12bβ]]-7-[(5-Thio-5-oxo-4,5,6-trihydro-cyclopenta[c]thiophene)methylamino]-3,4,6,7,8,12b-hexahydro-6-oxo-1H-[1,4]-thiazino[3,4-a][2]benzazepine-4-carboxylic acid, diphenylmethyl ester, (S)-N-(t-butoxycarbonyl)-1-(2-methylpropyl)- 2-(thio)-ethylamine, disulfide.

EXAMPLE 25

[4S-[4α, 7α(R*), 12bβ]]-7-[(5-Thio-5-oxo-2,4,5,6-tetrahydrocyclopenta[c]pyrrole)methylamino]-3,4,6,7,8,12b-hexahydro-6-oxo-1H-[1,4]-azazino[3,4-a][2]benzazepine-4-carboxylic acid, (S)-1-(2-methylpropyl)-2-(thio)-ethylamine, disulfide trifluoroacetic acid salt;

Scheme A, optional step b:

Prepare in a manner similar to Example 14 using [4S-[4α, 7α(R*), 12bβ]]-7-[(5-Thio-5-oxo-2,4,5,6-tetrahydro-cyclopenta[c]pyrrole)methylamino]-3,4,6,7,8,12b-hexahydro-6-oxo-1H-[1,4],azazino[3,4-a][2]benzazepine-4-carboxylic acid, diphenylmethyl ester, (S)-N-(t-butoxycarbonyl)-1-(2-methylpropyl)- 2-(thio)-ethylamine, disulfide.

EXAMPLE 26

[4S-[4α, 7α(R*), 12bβ]]-7-[(5-Thio-5-oxo-2,4,5,6-tetrahydro-cyclopenta[c]pyrrole)methylamino]-3,4,6,7,8,12b-hexahydro-6-oxo-1H-[1,4]-azazino[3,4-a][2]benzazepine-4-carboxylic acid, (S)-1-(2-methylpropyl)-2-(thio)-ethylamine, disulfide trifluoroacetic acid salt;

Scheme A, optional step b:

Prepare in a manner similar to Example 14 using [4S-[4α, 7α(R*), 12bβ]]-7-[(5-Thio-5-oxo-2,4,5,6-tetrahydro-cyclopenta[c]pyrrole)methylamino]-3,4,6,7,8,12b-hexahydro-6-oxo-1H-[1,4]-azazino[3,4-a][2]benzazepine-4-carboxylic acid, diphenylmethyl ester, (S)-N-(t-butoxycarbonyl)-1-(2-methylpropyl)-2-(thio)-ethylamine, disulfide.

EXAMPLE 27

[4S-[4α, 7α(R*), 12bβ]]-7-[(2-Thio-2-oxoindan)methylamino]-1,2,3,4,6,7,8,12b-octahydro-6-oxopyrido[2,1-a][2]benzazepine-4-carboxylic acid, diphenylmethyl ester, 2-thiopyridine, disulfide;

Scheme A, step a:

Combine [[4s-[4α, 7α(R*), 12bβ]]-7-[(2-Thio-2-oxoindan)methylamino]-1,2,3,4,6,7,8,12b-octahydro-6-oxopyrido[2,1-a][2]benzazepine-4-carboxylic acid, diphenylmethyl ester (4.0 mmol) and 2,2'-dithiodipyridine (16.0 mmol) in degassed ethanol (24 mL) and dichloromethane (6 mL). Stir under an inert atmosphere at ambient temperature for 20 hours. Evaporate in vacuo to obtain a residue. Chromatograph the residue on silica gel to give the title compound.

An alternate general synthetic procedure is set forth in Scheme B for preparing compounds of Formula (I). In Scheme B, all substituents unless otherwise indicated, are as previously defined. Starting materials, reagents, techniques, and procedures used in Scheme B are well known and appreciated by one of ordinary skill in the art.

SCHEME B

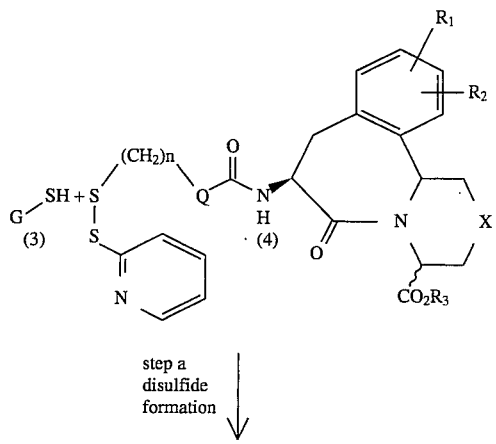

step a
disulfide
formation

-continued
SCHEME B

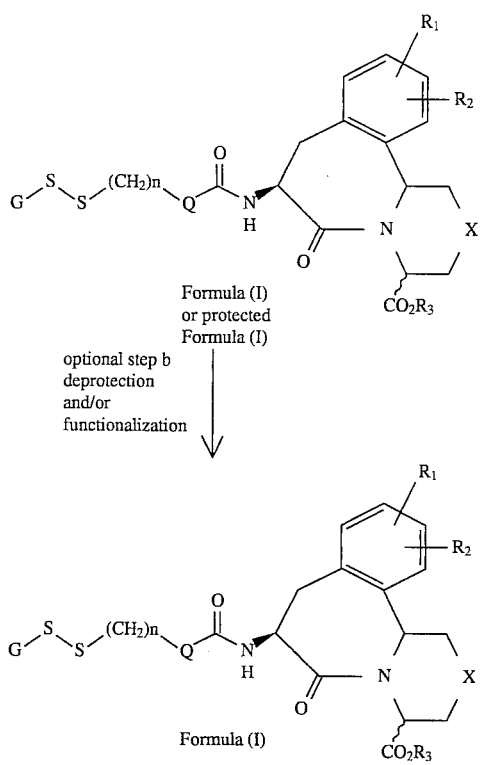

Formula (I)
or protected
Formula (I)

optional step b
deprotection
and/or
functionalization

Formula (I)

In Scheme B, step a, an appropriate thiol of structure (3) is contacted with an appropriate disulfide of structure (4) to give a disulfide of Formula (I) or a protected disulfide of Formula (I) by the method taught above in Scheme A, step a. An appropriate thiol of structure (3) is one in which G is as desired in the final product of Formula (I) or gives rise after deprotection to G as desired in the final product of Formula (I). An appropriate disulfide of the structure (4) is one in which $R_1$, $R_2$, $R_3$, Q, X, and n are as desired in the final product of Formula (I) or give rise after deprotection and/or functionalization to $R_1$, $R_2$, $R_3$, Q, and X as desired in the final product of Formula (I). An appropriate disulfide of structure (4) can be prepared by methods known analogously in the art, B. P. Roques et al, *J. Med. Chem.* 33, 2473–2481 (1992), from compounds of structure (2) which are known in the art; European Patent Application No. 0 534 363, published Mar. 31, 1993; or are known analogously in the art.

In Scheme B, optional step b, a protected disulfide of Formula (I) is deprotected to give a disulfide of Formula (I) as taught in Scheme A optional, step b above.

The following preparations and examples present typical syntheses as described in Scheme B. These preparations and examples are understood to be illustrative only and are not intended to limit the scope of the invention in any way. As used in the following preparations and examples, the following terms have the meanings indicated: "g" refers to grams, "mmol" refers to millimoles, "mL" refers to milliliters, "° C." refers to degrees Celsius, "$R_f$" refers to retention factor, "mp" refers to melting point, "dec" refers to decomposition, "M" refers to molar, and "TLC" refers to thin layer chromatography.

PREPARATION 4

2-Thiolaceticacid morpholine carboxamide; Preparation of starting material for Scheme B, step a:

Combine chloroacetyl chloride (2.00 mL, 25.0 mmol) and N-methylmorpholine (2.76 mL, 25.0 mmol) in dichloromethane (100 mL). Cool in an ice-bath. Add morpholine (2.19 mL, 25.0 mmol) and stir in the ice-bath for 1 hour. Warm to ambient temperature and stir for 1 hour. Extract with cold aqueous 5% sulfuric acid solution, saturated aqueous sodium bicarbonate solution, and saturated aqueous sodium chloride solution. Dry the organic layer over $Na_2SO_4$, filter, and evaporate in vacuo to obtain chloroacetic acid morpholine carboxamide.

Combine chloroacetic acid morpholine carboxamide prepared above (2.88 g, 17.6 mmol) and thiolacetic acid (1.40 mL, 20.0 mmol) in degassed dimethylformamide (10 mL). Slowly add cesium carbonate (3.26 g, 10.0 mmol) providing cooling as needed to keep the temperature of the reaction mixture below 40° C. Stir at ambient temperature for 16 hours. Partition the reaction mixture between water and ethyl acetate. Dry the organic layer over $Na_2SO_4$, filter, and evaporate in vacuo to obtain a residue. Chromatograph the residue on silica gel eluting sequentially with 40% ethyl acetate/hexane and then 66% ethyl acetate/hexane to give 2-acetylthioacetic acid morpholine carboxamide.

Combine 2-acetylthioacetic acid morpholine carboxamide obtained above (2.50 g, 12.0 mmol) and degassed methanol (50 mL). Cool in an ice-bath. Add lithium hydroxide hydrate ( 1.0 g,24.0 mmol). Stir for 3 hours. Acidify the reaction mixture to pH=1 with 6M hydrochloric acid solution. Partition the reaction mixture between water and dichloromethane. Extract the organic layer with saturated aqueous ammonium chloride solution. Dry the organic layer over $Na_2SO_4$, filter, and evaporate in vacuo to obtain a residue. Chromatograph the residue on silica gel eluting with ethyl acetate to give the title compound.

EXAMPLE 28

[4S-[4α, 7α(R*) 12bβ]]-7-[(2-Thio-2-oxoindan)methylamino]-1,2,3,4,6,7,8,12b-octahydro-6-oxopyrido[2,1-a][2]benzazepine-4-carboxylic acid, diphenylmethyl ester, N-(t-butoxycarbonyl)-L-cysteine ethyl ester, disulfide;

Scheme B, step a:

Combine [4S-[4α, 7α(R*), 12bβ]]-7-[(2-Thio-2-oxoindan)methylamino]-1,2,3,4,6,7,8,12b-octahydro-6-oxopyrido[2,1-a][2]benzazepine-4-carboxylic acid, diphenylmethyl ester, 2-thiopyridine, disulfide; the product of Example 27; (1.4 mmol) and N-(t-butoxycarbonyl)-L-cysteine ethyl ester (2.0 mmol) in degassed ethanol/dichloromethane (10 mL)/(2 mL). Stir for 18 hours. Evaporate in vacuo to obtain a residue. Chromatograph the residue on silica gel to give the title compound.

EXAMPLE 29

[4S-[4α, 7α(R*) 12bβ]]-7-[(2-Thio-2-oxoindan)methylamino]-1,2,3,4,6,7,8,12b-octahydro-6-oxopyrido[2,1-a][2]benzazepine-4-carboxylic acid, diphenylmethyl ester, benzylthio, disulfide;

Scheme B, step a:

Prepare in a manner similar to Example 28 using benzylthiol.

EXAMPLE 30

[4S-[4α, 7α(R*), 12bβ]]-7-[(2-Thio-2-oxoindan)methylamino]-1,2,3,4,6,7,8,12b-octahydro-6-oxopyrido[2,1-][2benzazepine-4-carboxylic acid, diphenylmethyl ester, ethylthio, disulfide;

Scheme B, step a:

Prepare in a manner similar to Example 28 using ethylthiol.

EXAMPLE 31

[4S-[4α, 7α(R*), 12bβ]]-7-[(2-Thio-2-oxoindan)methylamino]-1,2,3,4,6,7,8,12b-octahydro-6-oxopyrido[2,1-a][2]benzazepine-4-carboxylic acid, diphenylmethyl ester, 2-hydroxyethylthio, disulfide;

Scheme B, step a:

Prepare in a manner similar to Example 28 using 2-hydroxyethylthiol.

EXAMPLE 32

[4S-[4α, 7α(R*), 12bβ]]-7-[(2-Thio-2-oxoindan)methylamino]-1,2,3,4,6,7,8,12b-octahydro-6-oxopyrido[2,1-a][2]benzazepine-4-carboxylic acid, diphenylmethyl ester, 2-pyridylmethylthio, disulfide;

Scheme B, step a:

Prepare in a manner similar to Example 28 using 2-pyridylmethylthiol.

EXAMPLE 33

[4S-[4α, 7α(R*), 12bβ]]-7-[(2-Thio-2-oxoindan)methylamino]-1,2,3,4,6,7,8,12b-octahydro-6-oxopyrido[2,1-a][2]benzazepine-4-carboxylic acid, diphenylmethyl ester, 2-thioacetic acid morpholine carboxamide;

Scheme B, step a:

Prepare in a manner similar to Example 28 using thiolacetic acid morpholine carboxamide.

EXAMPLE 34

[4S-[4α, 7α(R*), 12bβ]]-7-[(2-Thio-2-oxoindan)methylamino]-1,2,3,4,6,7,8,12b-octahydro-6-oxopyrido[2,1-a][2]benzazepine-4-carboxylic acid, L-cysteine ethyl ester, disulfide trifluoroacetic acid salt;

Scheme B, optional step b:

Combine [4S-[4α, 7α(R*), 12bβ]]-7-[(2-Thio-2-oxoindan)methylamino]-1,2,3,4,6,7,8,12b-octahydro-6-oxopyrido[2,1-a][2]benzazepine-4-carboxylic acid, diphenylmethyl ester, N-(t-butoxycarbonyl)-L-cysteine ethyl ester, disulfide (1.31 mmol) anisole (1.4 mL, 13.0 mmol) and dichloromethane (15 mL). Cool in an ice-bath. Add trifluoroacetic acid (3 mL). Stir for 2 hours in the ice-bath and the warm to ambient temperature and stir an additional 2 hours. Evaporate in vacuo to obtain a residue. Add carbon tetrachloride to the residue and evaporate in vacuo to obtain a residue. Triturate with hexane, filter and dry in vacuo to give the title compound.

EXAMPLE 35

[4S-[4α, 7α(R*), 12bβ]]-7-[(2-Thio-2-oxoindan)methylamino]-1,2,3,4,6,7,8,12b-octahydro-6-oxopyrido[2,1-a][2]benzazepine-4-carboxylic acid, benzylthio, disulfide;

Scheme B, optional step b:

Prepare in a manner similar to Example 34 using [4S-[4α, 7α(R*), 12bβ]]-7-[(2-Thio-2-oxoindan)methylamino]-1,2,3,4,6,7,8,12b-octahydro-6-oxopyrido[2,1-a][2]benzazepine-4-carboxylic acid, diphenylmethyl ester, benzylthio, disulfide.

EXAMPLE 36

[4S-[4α, 7α(R*), 12bβ]]-7-[(2-Thio-2-oxoindan)methylamino]-1,2,3,4,6,7,8,12b-octahydro-6-oxopyrido[2,1-a][2]benzazepine-4-carboxylic acid, ethylthio, disulfide;

Scheme B, optional step b:

Prepare in a manner similar to Example 50 using [4S-[4α, 7α(R*), 12bβ]]-7-[(2-Thio-2-oxoindan)methylamino]-1,2,3,4,6,7,8,12b-octahydro-6-oxopyrido[2,1-a][2]benzazepine-4-carboxylic acid, diphenylmethyl ester, ethylthio, disulfide.

EXAMPLE 37

[4S-[4α, 7α(R*), 12bβ]]-7-[(2-Thio-2-oxoindan)methylamino]-2,3,4,6,7,8,12b-Octahydro-6-oxopyrido[2,1-a][2]benzazepine-4-carboxylic acid, 2-hydroxyethylthio, disulfide;

Scheme B, optional step b:

Prepare in a manner similar to Example 34 using [4S-[4α, 7α(R*), 12bβ]]-7-[(2-Thio-2-oxoindan)methylamino]-1,2,3,4,6,7,8,12b-octahydro-6-oxopyrido[2,1-a][2]benzazepine-4-carboxylic acid, diphenylmethyl ester, 2-hydroxyethylthio, disulfide.

EXAMPLE 38

[4S-[4α, 7α(R*),
12bβ]]-7-[(2-Thio-2-oxoindan)methylamino]-
1,2,3,4,6,7,8,12b-octahydro-6-oxopyrido[2,1-
a][2]benzazepine-4-carboxylic acid,
2-pyridylmethylthio, disulfide;

Scheme B, optional step b:

Prepare in a manner similar to Example 34 using [4S-[4α, 7α(R*), 12bβ]]-7-[(2-Thio-2-oxoindan)methylamino]-1,2,3,4,6,7,8,12b-octahydro-6-oxopyrido[2,1-a][2]benzazepine-4-carboxylic acid, diphenylmethyl ester, 2-pyridylmethylthio, disulfide.

EXAMPLE 39

[4S-[4α, 7α(R*),
12bβ]]-7-[(2-Thio-2-oxoindan)methylamino]-
2,3,4,6,7,8,12b-octahydro-6-oxopyrido[2,1-
a][2]benzazepine-4-carboxylic acid, 2-thioacetic
acid morpholine carboxamide, disulfide;

Scheme B, optional step b:

Prepare in a manner similar to Example 34 using [4S-[4α, 7α(R*), 12bβ]]-7-[(2-Thio-2-oxoindan)methylamino]-1,2,3,4,6,7,8,12b-octahydro-6-oxopyrido[2,1-a][2]benzazepine-4-carboxylic acid, diphenylmethyl ester, 2-thioacetic acid morpholine carboxamide, disulfide.

As used herein, the term "patient" refers to warm-blooded animals or mammals, including mice, rats and humans. A patient is in need of treatment to inhibit enkephalinase when the patient is suffering from acute or chronic pain and is in need of an endorphin- or enkephalin-mediated analgesic effect. In addition, a patient is in need of treatment to inhibit enkephalinase when the patient is suffering from a disease state characterized by abnormalities in fluid, electrolyte, blood pressure, intraocular pressure, renin, or aldosterone homeostasis, such as, but not limited to, hypertension, renal diseases, hyperaldosteronemia, cardiac hypertrophy, glaucoma and congestive heart failure. In these instances the patient is in need of an ANP-mediated diuretic, natriuretic, hypotensive, hypoaldosteronemic effect. Inhibition of enkephalinase would provide an endorphin- or enkephalin-mediated analgesic effect by inhibiting the metabolic degradation of endorphins and enkephalins. Inhibition of enkephalinase would provide an ANP-mediated diuretic, natriuretic, hypotensive, hypoaldosteronemic effect by inhibiting the metabolic degradation of ANP. Inhibition of enkephalinase would also modulate intestinal smooth muscle contractility and would be useful in the treatment of irritable bowel syndrome.

In addition, a patient is in need of treatment to inhibit enkephalinase when the patient is in need of an antidepressant effect or a reduction in severity of withdrawal symptoms associated with termination of opiate or morphine administration.

The identification of those patients who are in need of treatment to inhibit enkephalinase is well within the ability and knowledge of one skilled in the art. A clinician skilled in the art can readily identify, by the use of clinical tests, physical examination and medical/family history, those patients who are in need of an endorphin- or enkephalin-mediated analgesic effect or who are in need of an ANP-mediated diuretic, natriuretic, hypotensive or hypoaldosteronemic effect.

An effective enkephalinase inhibitory amount of a compound of Formula (I) is an amount which is effective in inhibiting enkephalinase and in thus inhibiting the metabolic degradation of the naturally-occurring circulating regulatory peptides such as the endorphins, including enkephalins, and ANP. Successful treatment is also understood to include prophylaxis in treating a patient in those instances such as, for example, in a pre-operative procedure, where a patient will be suffering from acute or chronic pain in the near future.

An effective enkephalinase inhibitory amount of a compound of Formula (I) is an amount which is effective in inhibiting enkephalinase in a patient in need thereof which results, for example, in endorphin- or enkephalin-mediated analgesic effects or in ANP-mediated diuretic, natriuretic, hypotensive, hypoaldosteronemic effect.

An effective enkephalinase inhibitory dose can be readily determined by the use of conventional techniques and by observing results obtained under analogous circumstances. In determining the effective dose, a number of factors are considered including, but not limited to: the species of patient; its size, age, and general health; the specific disease involved; the degree of or involvement or the severity of the disease; the response of the individual patient; the particular compound administered; the mode of administration; the bioavailability characteristics of the preparation administered; the dose regimen selected; and the use of concomitant medication.

An effective enkephalinase inhibitory amount of a compound of Formula (I) will generally vary from about 0.01 milligram per kilogram of body weight per day (mg/kg/day) to about 20 mg/kg/day. A daily dose of from about 0.1 mg/kg to about 10 mg/kg is preferred.

In addition, the present invention further provides a method of inhibiting ACE in a patient in need thereof comprising administering to said patient an effective ACE inhibitory amount of a compound of Formula (I). A patient is in need of treatment to inhibit ACE when the patient is suffering from hypertension, chronic congestive heart failure, hyperaldosteronemia or cognitive disorders. Inhibition of ACE reduces levels of angiotensin II and thus inhibits the vasopressor, hypertensive and hyperaldosteronemic effects caused thereby. An effective ACE inhibitory amount of a compound of Formula (I) is that amount which is effective in inhibiting ACE in a patient in need thereof which results, for example, in a hypotensive effect. An effective ACE inhibitory amount and an effective ACE inhibitory dose are the same as that described above for an effective enkephalinase inhibitory amount and dose.

In addition, the present invention further provides a method for treating a patient suffering from smooth cell proliferation. An effective smooth cell proliferation inhibitory amount of a compound of Formula (I) is that amount which is effective in inhibiting smooth cell proliferation in a patient in need thereof which results, for example, in a reduced myointimal thickening after vascular injury. An effective smooth cell proliferation inhibitory amount and an effective smooth cell proliferation inhibitory dose are the same as that described above for an effective enkephalinase inhibitory amount and dose.

In effecting treatment of a patient, compounds of Formula (I) can be administered in any form or mode which makes the compound bioavailable in effective amounts, including oral and parenteral routes. For example, the compound can be administered orally, subcutaneously, intramuscularly, intravenously, transdermally, intranasally, rectally, and the like. Oral administration is generally preferred. One skilled in the art of preparing Formulations can readily select the proper form and mode of administration depending upon the disease state to be treated, the stage of the disease, and other relevant circumstances.

Compounds of Formula (I) can be administered in the form of pharmaceutical compositions or medicaments which are made by combining the compounds of Formula (I) with pharmaceutically acceptable carriers or excipients, the proportion and nature of which are determined by the chosen route of administration, and standard pharmaceutical practice.

In another embodiment, the present invention provides compositions comprising a compound of Formula (I) in admixture or otherwise in association with one or more inert carriers. These compositions are useful, for example, as assay standards, as convenient means of making bulk shipments, or as pharmaceutical compositions. An assayable amount of a compound of Formula (I) is an amount which is readily measurable by standard assay procedures and techniques as are well known and appreciated by those skilled in the art. Assayable amounts of a compound of Formula (I) will generally vary from about 0.001% to about 75% of the composition by weight. Inert carriers can be any material which does not degrade or otherwise covalently react with a compound of Formula (I). Examples of suitable inert carriers are water; aqueous buffers, such as those which are generally useful in High Performance Liquid Chromatography (HPLC) analysis; organic solvents, such as acetonitrile, ethyl acetate, hexane and the like; and pharmaceutically acceptable carriers or excipients.

More particularly, the present invention provides pharmaceutical compositions comprising an effective amount of a compound of Formula (I) in admixture or otherwise in association with one or more pharmaceutically acceptable carriers or excipients.

The pharmaceutical compositions or medicaments are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral or parenteral use and may be administered to the patient in the form of tablets, capsules, suppositories, solution, suspensions, or the like.

The pharmaceutical compositions may be administered orally, for example, with an inert diluent or with an edible carrier. They may be enclosed in gelatin capsules or compressed into tablets. For the purpose of oral therapeutic administration, the compounds of Formula (I) may be incorporated with excipients and used in the form of tablets, troches, capsules, elixirs, suspensions, syrups, wafers, chewing gums and the like. These preparations should contain at least 4% of the compound of Formula (I), the active ingredient, but may be varied depending upon the particular form and may conveniently be between 4% to about 70% of the weight of the unit. The amount of the active ingredient present in compositions is such that a unit dosage form suitable for administration will be obtained.

The tablets, pills, capsules, troches and the like may also contain one or more of the following adjuvants: binders, such as microcrystalline cellulose, gum tragacanth or gelatin; excipients, such as starch or lactose, disintegrating agents such as alginic acid, Primogel, corn starch and the like; lubricants, such as magnesium stearate or Sterotex; glidants, such as colloidal silicon dioxide; and sweetening agents, such as sucrose or saccharin may be added or flavoring agents, such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active ingredient, sucrose as a sweetening agent and certain preservatives, dyes and colorings and flavors. Materials used in preparing these various compositions should be pharmaceutically pure and non-toxic in the amounts used.

For the purpose of parenteral administration, the compounds of Formula (I) may be incorporated into a solution or suspension. These preparations should contain at least 0.1% of a compound of the invention, but may be varied to be between 0.1 and about 50% of the weight thereof. The amount of the active ingredient present in such compositions is such that a suitable dosage will be obtained.

The solutions or suspensions may also include one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of toxicity such as sodium chloride or dextrose. The parenteral preparation can be enclosed in ampules, disposable syringes or multiple dose vials made of glass or plastic.

As with any group of structurally related compounds which possess a particular generic utility, certain groups and configurations are preferred for compounds of Formula (I) in their end-use application. The compounds of Formula (I) wherein $R_1$ is hydrogen or alkoxy are preferred. The compounds of Formula (I) wherein $R_2$ is hydrogen or alkoxy are preferred. The compounds of Formula (I) wherein n is 0 are preferred. The compounds of Formula (I) wherein $R_3$ is hydrogen are preferred. The compounds of Formula (I) wherein Q is

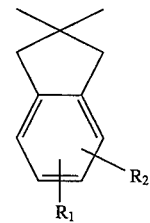

are preferred.

It is, of course, understood that the compounds of Formula (I) may exist in a variety of isomeric configurations including structural as well as stereo isomers. It is further understood that the present invention encompasses those compounds of Formula (I) in each of their various structural and stereo isomeric configurations as individual isomers and as mixtures of isomers.

The following specific compounds of Formula (I) are particularly preferred in the end-use application of the compounds of the present invention:

[4S-[4α, 7α(R*), 12bβ]]-7-[(2-Thio-2-oxoindan)methylamino]-1,2,3,4,6,7,8,12b-octahydro-6-oxopyrido [2,1-a][2]benzazepine-4-carboxylic acid, (S)-1-(2-methylpropyl)-2-(thio)-ethylamine, disulfide;

[4S-[4α, 7α(R*), 12bβ]]-7-[(2-Thio-2-oxoindan)methylamino]-1,2,3,4,6,7,8,12b-octahydro-6-oxopyrido [2,1-a] [2]benzazepine-4-carboxylic acid, (R)-1-(2-methylpropyl)-2-(thio)-ethylamine, disulfide;

[4S-[4α, 7α(R*), 12bβ]]-7-[(2-Thio-2-oxoindan)methylamino]-1,2,3,4,6,7,8,12b-octahydro-6-oxopyrido [2,1-a] [2]benzazepine-4-carboxylic acid, pivaloyloxymethyl ester, (S)-1-(2-methylpropyl)-2-(thio)-ethylamine, disulfide;

[4S-[4α, 7α(R*), 12bβ]]-7-[(2-Thio-2-oxoindan)methylamino]-1,2,3,4,6,7,8,12b-octahydro-6-oxopyrido [2,1-a] [2]benzazepine-4-carboxylic acid, L-cysteine ethyl ester, disulfide;

[4S-[4α, 7α(R*), 12bβ]]-7-[(2-Thio-2-oxoindan)methylamino]-1,2,3,4,6,7,8,12b-octahydro-6-oxopyrido [2,1-a] [2]benzazepine-4-carboxylic acid, N-acetyl-L-cysteine, disulfide;

[4S-[4α, 7α(R*), 12bβ]]-7-[(2-Thio-2-oxoindan)methylamino]-1,2,3,4,6,7,8,12b-octahydro-6-oxopyrido [2,1-a] [2]benzazepine-4-carboxylic acid, L-cysteine, disulfide;

[4S-[4α, 7α(R*), 12bβ]]-7-[(2-Thio-2-oxoindan)methylamino]-1,2,3,4,6,7,8,12b-octahydro-6-oxopyrido [2,1-a] [2]benzazepine-4-carboxylic acid, benzylthio, disulfide;

[4S-[4α, 7α(R*), 12bβ]]-7-[(2-Thio-2-oxoindan)methylamino]-1,2,3,4,6,7,8,12b-octahydro-6-oxopyrido [2,1-a] [2]benzazepine-4-carboxylic acid, ethylthio, disulfide;

4S-[4α, 7α(R*), 12bβ]]-7-[(2-Thio-2-oxoindan)methylamino]-1,2,3,4,6,7,8,12b-octahydro-6-oxopyrido[2,1-a] [2]benzazepine-4-carboxylic acid, 2-hydroxyethylthio, disulfide;

4S-[4α, 7α(R*), 12bβ]]-7-[(2-Thio-2-oxoindan)methylamino]-1,2,3,4,6,7,8,12b-octahydro-6-oxopyrido[2,1-a] [2]benzazepine-4-carboxylic acid, 2-pyridylmethyl, disulfide;

4S-[4α, 7α(R*), 12bβ]]-7-[(2-Thio-2-oxoindan)methylamino]-1,2,3,4,6,7,8,12b-octahydro-6-oxopyrido[2,1-a] [2]benazepine-4-carboxylic acid, 2-thioacetic acid morpholine carboxamide, disulfide.

The following in vivo and ex vivo studies illustrate the utility of the compounds of the present invention as enkephalinase inhibitors and as ACE inhibitors. These studies are carried out by the method of J. F. French et al *J. Pharmcacol. Exp. Ther.*, 268(1), 180–186 (1994).

Administer test compound or vehicle (99/1, ethanol/1% sodium bicarbonate solution) to fasted male Sprague-Dawley rats (Charles Rivers Breeding Laboratories Inc.). Administration is carried out by intraperitoneal injection. At 3 hours after administration, sacrifice the rats and remove the kidneys and freeze. Homogenize whole kidneys and carry through the P2 step of the protocol of Booth and Kenny [*Biochem. J.*, 142, 575–581 (1974)] for the preparation of the microvilli fraction. Resuspend P2 material in 50 mM HEPES buffer, pH 8.0, containing 0.3M NaCl and 0.5% Triton X-100 and keep at −20° C. prior to the assay. The enzyme activity may be measured by the fluorometric methods of Florentin et al *Anal. Biochem.* 141, 62–69 (1984). The enzyme is assayed in 50 mM HEPES buffer (pH 7.4) in a 3.0 mL reaction volume containing 12 μM of the substrate dansyl-D-AlaGly(p-nitro)PheGly-OH ($K_m$=40 μM) at 25° C. The enzyme in a small volume is added to initiate the reaction and the rate of fluorescence increase is recorded continuously using a fluorometer (excitation at 339 nm, emission at 562 nm). Use Thiorphan (Sigma Chemical Co.) as a standard for NEP inhibition in vitro. The effectiveness of the test compound is determined by measuring enzyme activity from kidneys obtained from test compound treated rats compared to enzyme activity from kidneys obtained from vehicle treated rats. The Thiorphan treated animals serve as a positive control. Determine ACE activity by the radiometric assay method of Ryan [J. W. Ryan, *Methods in Enzymatic Analysis*, 3rd ed., vol. 5, p. 20–34; ed. by J. Bergmeyer and M. Grassi, Verlag Chemie, Weinheim 1983], using tritiated hippuryl-glycyl-glycine (Ventrex Laboratories, Portland Me.). Buffer is used in the spectrophotometric ACE assay. After acid quench, tritiated product is extracted into Ventrex Cocktail 1 [B. N. Swanson etal, *Anal. Biochem.* 148, 401–407 (1985)]and count in a Beckman scintillation counter. Complete inhibition of radioactive product formation by 1 μM enalaprilat in the assay of either compound- or vehicle-dosed rat kidney preparations is taken to demonstrate specificity for ACE.

Anesthetize Sprague-Dawley male rats (Charles Rivers Breeding Laboratories Inc.) weighing 230–290 g with methoxyfluorane and pith by inserting a stainless steel rod (2.2 mm in diameter) through the right eye socket, through the brain and down the spinal column to the sacral region. Ventilate the rat's lungs through an endotracheal tube (Harvard Pump, Model 688). Ventilate at a rate of 12.5 mL/minute provided in 50 strokes. Record systemic blood pressure from a cannula (PE 50, containing 0.01% heparin) inserted into the left carotid artery and attached to a pressure transducer (P23 DC). Systemic blood pressure is recorded continuously during the test on a polygraph (Grass Model 70). Insert a 23 G hypodermic needle attached to a cannula (PE 50) into the lumen of the right femoral vein for injection of the test compound. Thirty minutes after pithing, give an intravenous injection of angiotensin I (0.3 μg). Angiotensin I (human) is made up in 0.01% ascorbic acid solution at a concentration of 0.3 μg/mL from a stock solution of 550 μg/mL in 0.01% acetic acid solution. Repeat the intravenous injection of angiotensin I (0.3 μg) at 10 minute intervals until two consecutive injections give responses that are within 10% of each other. Administer by intraperitoneal or by intravenous injection, either the test compound or vehicle. Administer an intravenous injection of angiotensin I (0.3 μg) at 15, 30, 45, 60, 90, and 120 minutes following administration of test compound or vehicle. The effectiveness of the test compound is determined by measuring the decrease in angiotensin I induced pressor response for test compound treated rats compared to vehicle treated rats.

What is claimed is:

1. A compound of the formula

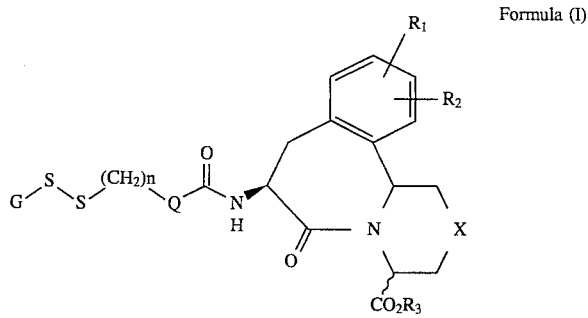

Formula (I)

wherein n is an integer from 0 to 3;

$R_1$ and $R_2$ are each time taken independently chosen from the group consisting of; hydrogen, hydroxy, —$OR_4$ wherein $R_4$ is a $C_1$-$C_4$ alkyl or an Ar—Y— group wherein Ar is a phenyl or naphthyl group unsubstituted or substituted with from one to three substituents selected from the group consisting of methylenedioxy, hydroxy, $C_1$-$C_4$ alkoxy, fluoro and chloro and Y is a $C_0$–$C_4$ alkyl; or, where $R_1$ and $R_2$ are attached to adjacent carbon atoms, $R_1$ and $R_2$ can be taken together with said adjacent carbons to form a benzene ring or methylenedioxy;

$R_3$ is hydrogen, $C_1$–$C_4$ alkyl, —$CH_2O$—$C(O)C(CH_3)_3$;

X is —$(CH_2)_p$—, O, S, $NR_5$, or $NC(O)R_6$ wherein p is an integer 0 or 1, $R_5$ is hydrogen, a $C_1$–$C_4$ alkyl, or an Ar—Y— group, and $R_6$ is —$CF_3$, $C_1$–$C_{10}$ alkyl, or an Ar—Y— group;

Q is chosen from the group

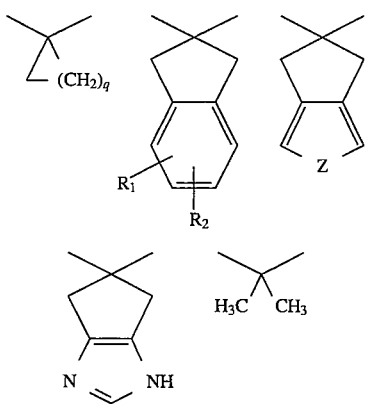

wherein q is an integer from 1 to 5 and Z is O, S, NH;

G is a radical chosen from the group;

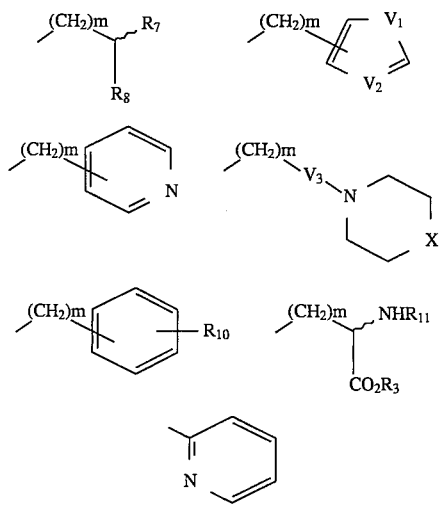

wherein m is an integer from 1 to 3;

$R_7$ is hydrogen, $C_1$–$C_6$ alkyl, —$CH_2CH_2S(O)_kCH_3$, or Ar—Y— wherein k is an integer form 0 to 2;

$R_8$ is hydrogen, hydroxy, amino, $C_1$–$C_6$ alkyl, N—methylamino, N,N-dimethylamino, —$CO_2R_3$ —$OC(O)R_9$ wherein $R_9$ is hydrogen, $C_1$–$C_6$ alkyl, or phenyl;

$R_{10}$ is 1 or 2 substituents independently chosen from the group consisting of; hydrogen, $C_1$–$C_4$ alkyl, $C_1$–$C_4$ alkoxy, or halogen;

$R_{11}$ is hydrogen, $C_1$–$C_6$ alkyl, or Ar—Y— group;

$V_1$ is O, S, or NH;

$V_2$ is N or CH;

$V_3$ is a direct bond or —C(O)—;

or stereoisomers or pharmaceutically acceptable salts thereof.

2. A compound of claim 1 wherein Q is

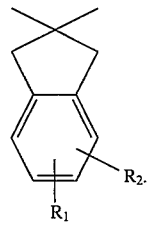

3. A compound of claim 2 wherein $R_3$ is hydrogen.

4. A compound of claim 2 wherein $R_1$ and $R_2$ are hydrogen.

5. A compound of claim 1 wherein the compound is [4S-[4α, 7α(R*), 12bβ]]-7-[(2-Thio-2-oxoindan)methylamino]-1,2,3,4,6,7,8,12b-octahydro-6-oxopyrido[2,1-a][2]benzazepine-4-carboxylic acid (S)-1-(2-methylpropyl)-2-(thio)-ethylamine, disulfide.

6. A compound of claim 1 wherein the compound is [4S-[4α, 7α(R*), 12bβ]]-7-[(2-Thio-2-oxoindan)methylamino]-1,2,3,4,6,7,8,12b-octahydro-6-oxopyrido[2,1-a][2]benzazepine-4-carboxylic acid, L-cysteine ethyl ester, disulfide.

7. A compound of claim 1 wherein the compound is [4S-[4α, 7α(R*), 12bβ]]-7-[(2-Thio-2-oxoindan)methylamino]-1,2,3,4,6,7,8,12b-octahydro-6-oxopyrido[2,1-a][2]benzazepine-4-carboxylic acid, benzylthio, disulfide.

8. A compound of claim 1 wherein the compound is [4S-[4α, 7α(R*), 12bβ]]-7-[(2-Thio-2-oxoindan)methylamino]- 1,2,3,4,6,7,8,12b-octahydro-6-oxopyrido[2,1-a][2]benzazepine-4-carboxylic acid, ethylthio, disulfide.

9. A compound of claim 1 wherein the compound is [4S-[4α, 7α(R*), 12bβ]]-7-[(2-Thio-2-oxoindan)methylamino]-1,2,3,4,6,7,8,12b-octahydro-6-oxopyrido[2,1-a][2]benzazepine-4-carboxylic acid, 2-hydroxyethylthio, disulfide.

10. A compound of claim 1 wherein the compound is [4S-[4α, 7α(R*), 12bβ]]-7-[(2-Thio-2-oxoindan)methylamino]-1,2,3,4,6,7,8,12b-octahydro-6-oxopyrido[2,1-a][2]benzazepine-4-carboxylic acid, 2-pyridylmethyl, disulfide.

11. A compound of claim 1 wherein the compound is [4S-[4α, 7α(R*), 12bβ]]-7-[(2-Thio-2-oxoindan)methylamino]-1,2,3,4,6,7,8,12b-octahydro-6-oxopyrido[2,1-a][2]benzazepine-4-carboxylic acid, 2-thioacetic acid morpholine carboxamide, disulfide.

* * * * *

UNITED STATES PATENT AND TRADEMARK OFFICE
CERTIFICATE OF CORRECTION

PATENT NO. : 5,567,814

DATED : October 22, 1996

INVENTOR(S) : Gary A. Flynn, et al.

It is certified that error appears in the above-identified patent and that said Letters Patent is hereby corrected as shown below:

At column 6, lines 42, 46 and 50, the patent reads "6-oxopyrido-6-oxopyrido[2,1-a]" and should read --6-oxopyrido[2,1-a]-- .
At column 7, lines 2 and 7, the patent reads "cyclopental" and should read --cyclopenta-- .
At column 7, line 11, the patent reads "-6-[(5-Thio" and should read -- -6-[(S)-(5-Thio --.
At column 7, lines 12 and 17, the patent reads "hexahydro" and should read --heptahydro--.
At column 11, lines 37 and 49 and column 12, line 5, the patent reads "-4carboxylic" and should read -- -4-carboxylic --.
At column 13, line 23, the patent reads "-7-[(2-Thioacetate" and should read -- -7-[(2-(2-Thioacetate --.
At column 14, line 18, the patent reads "carboxyiic" and should read --carboxylic--.
At column 14, line 27, the patent reads "[4S-[α," and should read -- [4S-[4α, --.
At column 14, line 31, the patent reads "-4carboxylic" and should read -- -4-carboxylic --.
At column 15, line 25, the patent reads "[2,1a-" and should read -- [2,1-a] -- .
At column 15, line 37, the patent reads "benezazepine" and should read --benzazepine--.
At column 16, line 37, the patent reads "[4s[4α," and should read -- [4S-[4α, --.
At column 16, line 58, the patent reads "1,2,3,4,5" and should read --1,2,3,5--.
At column 16, line 59, the patent reads "[2,1-a][2,1-a]benzazepine" and should read --[2,1-a][2]benzazepine--.
At column 17, line 41, the patent reads "1,2,3,46," and should read --1,2,3,4,6,--.
At column 19, line 36, the patent reads "EXAMPLE 1" and should read --EXAMPLE 11--.
At column 20, line 38-39, the patent reads "-6-pxpomdan)methylamino]2,1-a]" and should read -- -6-oxopyrido[2,1-a] --.

UNITED STATES PATENT AND TRADEMARK OFFICE
CERTIFICATE OF CORRECTION

PATENT NO. : 5,567,814

DATED : October 22, 1996

INVENTOR(S) :
Gary A. Flynn, et al.

It is certified that error appears in the above-identified patent and that said Letters Patent is hereby corrected as shown below:

At column 21, line 6, the patent reads "[2,1]" and should read --[2]--.
At column 22, line 21, the patent reads "4,5,6," and should read --4,6--.
At column 23, line 37, the patent reads "[1,4],azazino" and should read --[1,4]-azazino
At column 28, line 58 and column 29, line 20, the patent reads "2,3," and should read --1,2,3--.

Signed and Sealed this

Twentieth Day of October, 1998

Attest:

BRUCE LEHMAN

Attesting Officer

Commissioner of Patents and Trademarks